United States Patent
Kaneko et al.

(10) Patent No.: US 8,350,024 B2
(45) Date of Patent: Jan. 8, 2013

(54) SUGAR DERIVATIVES AND APPLICATION OF SAME

(76) Inventors: Tatsuo Kaneko, Nomi (JP); Maiko Kaneko, Nomi (JP)

(*) Notice: Subject to any disclaimer, the term of this patent is extended or adjusted under 35 U.S.C. 154(b) by 429 days.

(21) Appl. No.: 12/311,476

(22) PCT Filed: May 25, 2007

(86) PCT No.: PCT/JP2007/061229
§ 371 (c)(1),
(2), (4) Date: Apr. 29, 2009

(87) PCT Pub. No.: WO2008/062574
PCT Pub. Date: May 29, 2008

(65) Prior Publication Data
US 2010/0006801 A1   Jan. 14, 2010

(30) Foreign Application Priority Data
Nov. 22, 2006   (JP) ................................ 2006-316337

(51) Int. Cl.
*A61K 31/715* (2006.01)
*A61K 31/737* (2006.01)
*A61K 31/738* (2006.01)
*C08B 37/00* (2006.01)
*C08B 5/06* (2006.01)
*C07H 5/06* (2006.01)

(52) U.S. Cl. ........................ 536/55.1; 514/54; 536/123.1

(58) Field of Classification Search .................. None
See application file for complete search history.

(56) References Cited

FOREIGN PATENT DOCUMENTS

| JP | 11-092501 | 4/1999 |
|---|---|---|
| JP | 2001-224959 | 8/2001 |
| JP | 2005-047978 | 2/2005 |
| JP | 2006-188697 | 7/2006 |

OTHER PUBLICATIONS

Fujishiro et al., "Establishment of a Pure Culture of the Hitherto Uncultured Unicellular Cyanobacterium Aphanothece sacrum, and Phylogenetic Position of the Organism" Applied and Environmental Microbiology (2004) vol. 70 No. 6, pp. 3338-3345.*
Okajima-Kaneko et al., "Macroscopic birefringence in liquid crystals from novel cyanobacterial polysaccharide with an extremely high molecular weight" Proceedings of SPIE vol. 6587 (Liquid Crystals and Applications in Optics) May 9, 2007, pp. 1-8.*
Kiyotaka Kabata et al., "Suizenjinori no Baiyo Oyobi Kinosei Shokuhin to shite no Kanosei", The Japanese Society of Nutrition and Food Science Nishi Nippon SHibu Taikai Program Koen Yoshishu, 2003, p. 33.
Kiyotaka Kabata et al., "Nippon Koyushu Ranso Suizenjinori no Seibun to Kinosei", Japan Society for Bioscience, Biotechnology, and Agrochemistry Kansai Shibu Koenkai Koen Yoshishu, 2005, p. 75.

* cited by examiner

*Primary Examiner* — Eric S Olson
(74) *Attorney, Agent, or Firm* — Jordan and Hamburg LLP

(57) ABSTRACT

A sugar derivative derived from Aphanothece sacrum as a freshwater blue-green alga, having a mean molecular weight of 2,000,000 or more and a repeat structure of a sugar chain unit where a sugar constituent of a hexose structure and a sugar constituent of a pentose structure are conjugated together in a linear chain or a branched chain, containing a lactated, sulfated sugar as a constituent, where 2.7 or more hydroxyl groups per 100 hydroxyl groups are sulfated or sulfur element occupies 1.5% by weight or more of all of the elements, in the sugar chain unit. A sugar derivative with a novel polysaccharide structure as derived from Aphanothece sacrum is provided in such manner.

5 Claims, 25 Drawing Sheets

FIG. 2
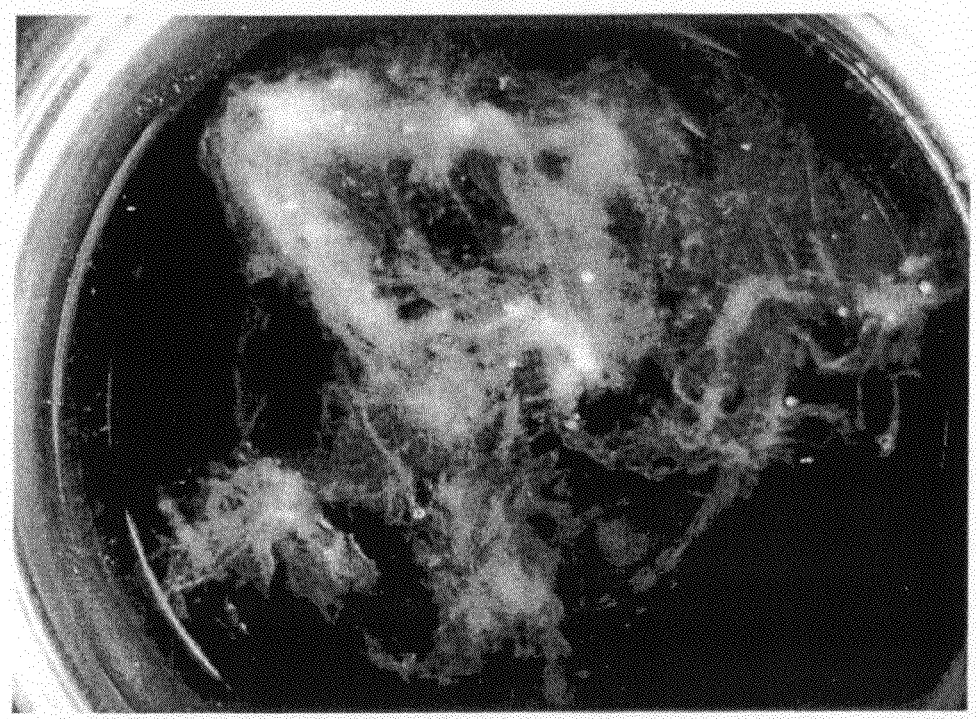
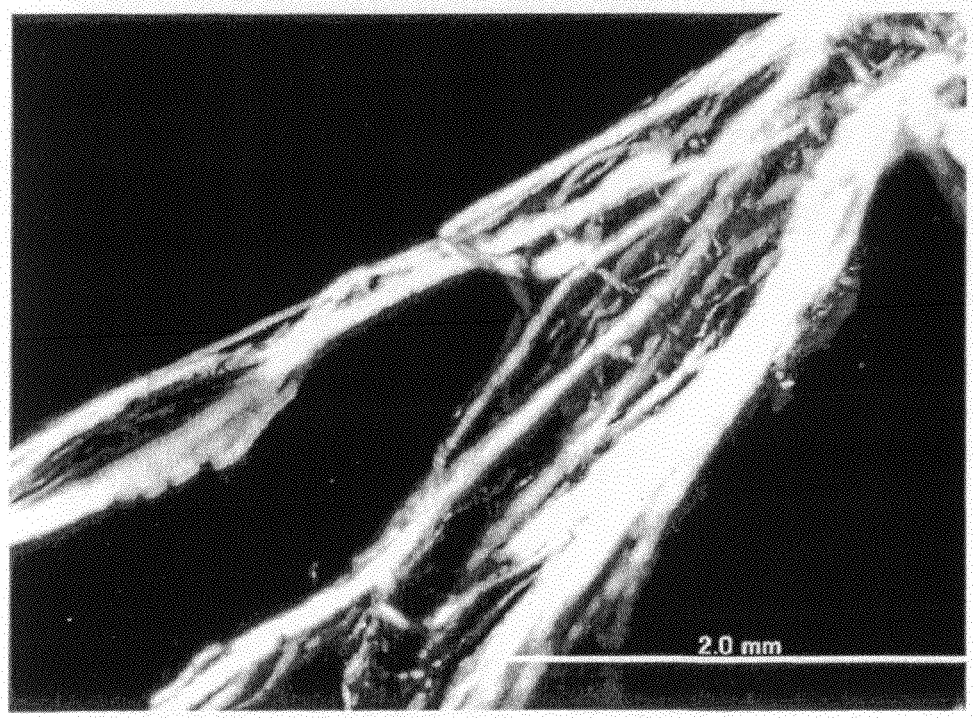

FIG. 5
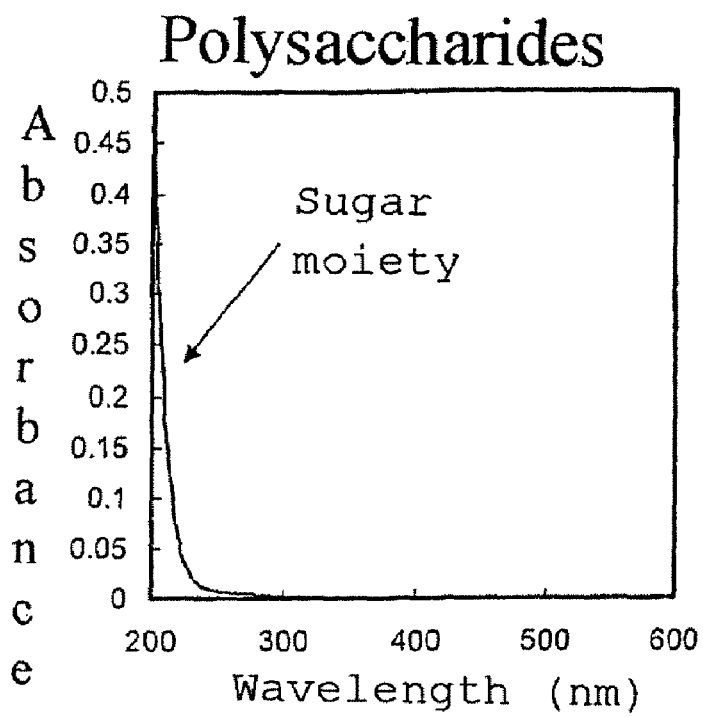
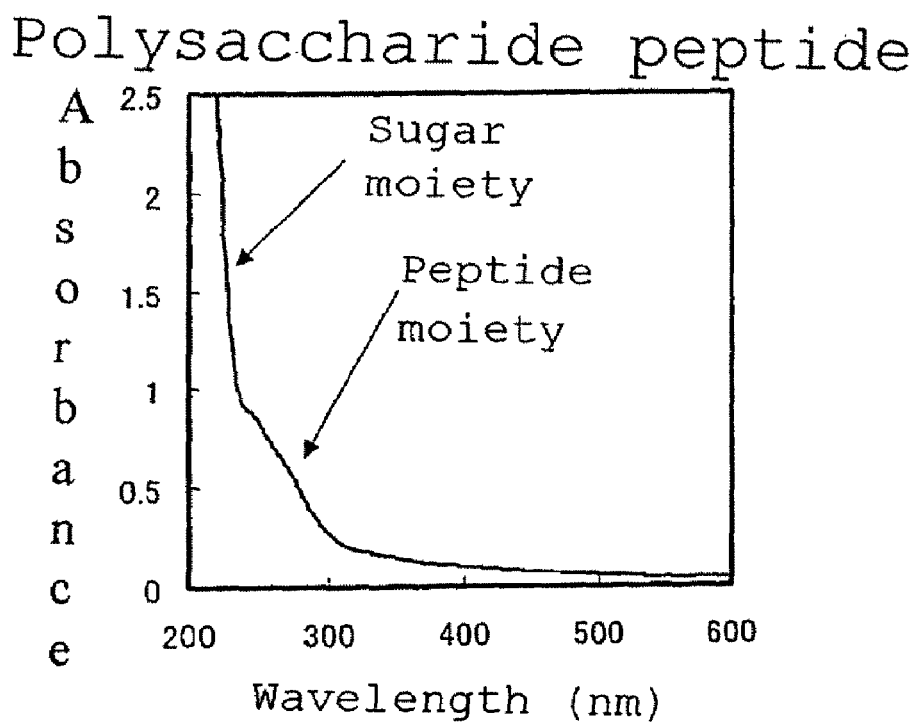

[FIG. 10]
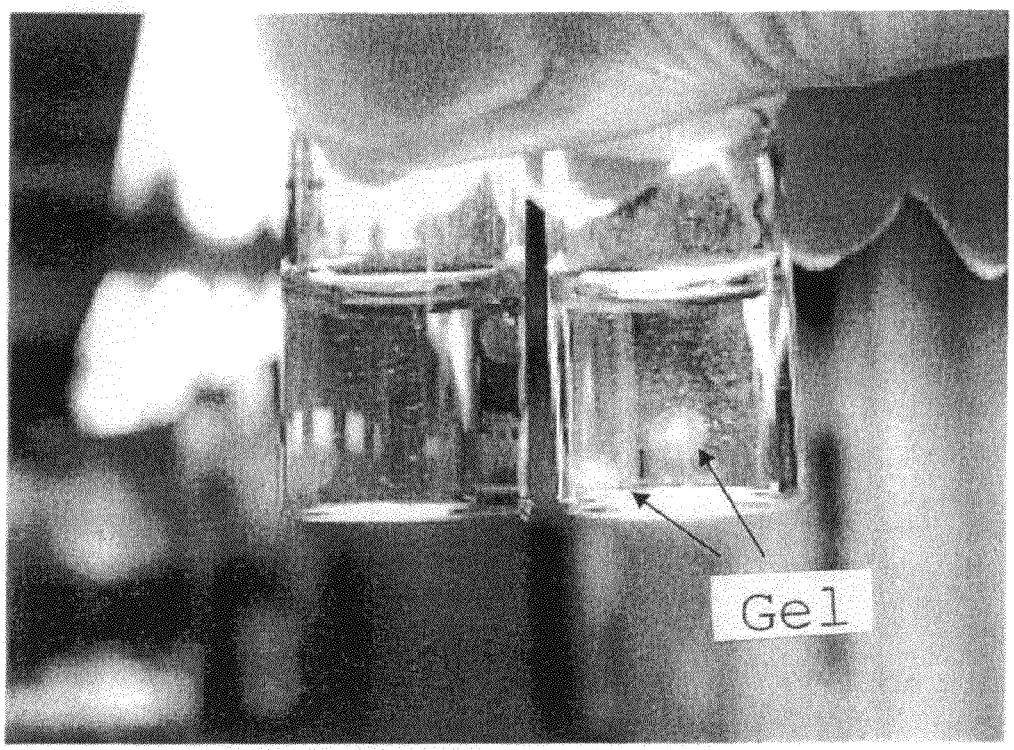
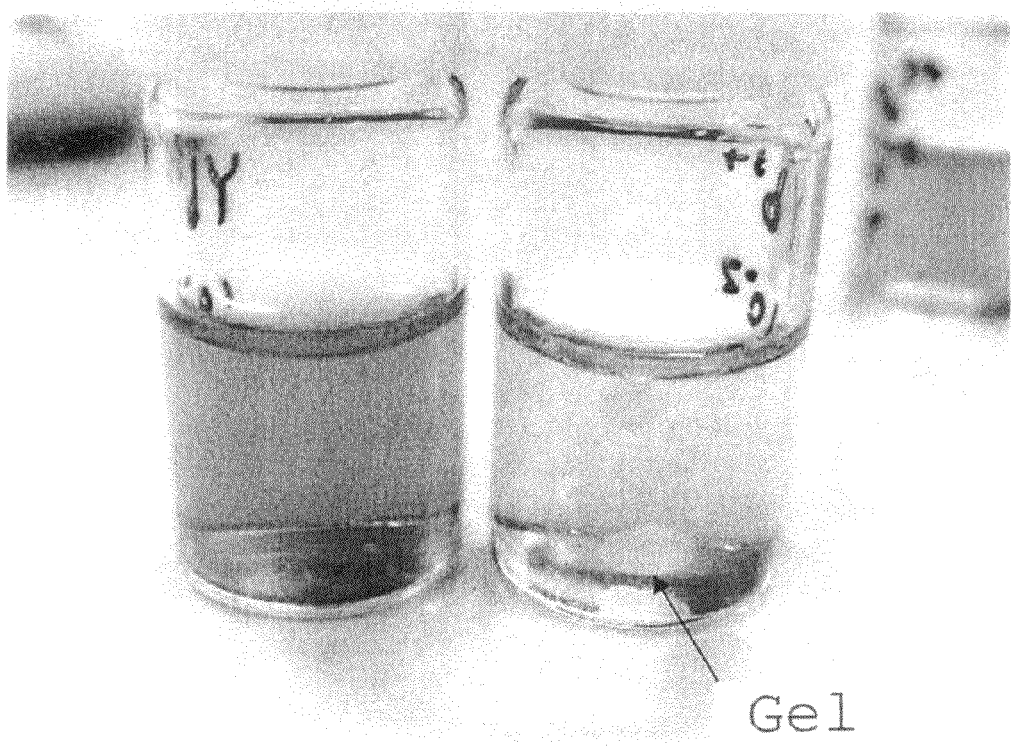

FIG. 22

| Table 1 m/z values of main peaks in milli-MS measuremnet and corresponding sugars ||||| 
|---|---|---|---|---|
| entry | m/z | m/z + H (MS:1.0078) | Sugar constituents | sugar MS |
| 1 | 278.124 | 279.1318 | dimethylmuramic acid | 279.132 |
| 2 | 287.0445 | 288.0523 | sulfated dimethylhexose | 288.052 |
| 3 | 358.0819 | 359.0897 | sulfated dimethylmuramic acid | 359.089 |
| 4 | 301.0239 | 302.0317 | sulfated dimethyluronic acid | 302.031 |
| 5 | 355.1241 | 356.1319 | methyl(hexose+hexose) | 356.132 |
| 6 | 435.0805 | 436.0883 | sulfated methyl(hexose+hexose) | 436.089 |
| 7 | 463.0773 | 464.0851 | sulfated dimethyl(hexose+uronic acid) | 464.084 |
| 8 | 630.2163 | 631.2241 | methyl(hexose+hexose+N-acetylmuramic acid) | 631.232 |

FIG. 24

| sample | 50 % Growth Inhibitory Concentration | | | $CC_{50}/IC_{50}$ selection index | |
|---|---|---|---|---|---|
| | $CC_{50}$ (mg/ml) (against host cells) | $IC_{50}$ (mg/ml) (against virus) | | | |
| | | pre-infection | post-infection | pre-infection | post-infection |
| Alkali-extracted sample | > 10,000 | 0.88 | 6.1 | > 11,000 | > 1,600 |
| Sample extracted at high pressure and high temperature | > 10,000 | 0.59 | 3.1 | > 17,000 | > 3,200 |

FIG. 25

| Sample | Concentration (mg/ml) | | | |
|---|---|---|---|---|
|  | 0.2 | 2 | 20 | 200 |
| Alkali-extracted sample | 84* | 67 | 53 | 48 |
| Sample extracted at high pressure and high temperature | 69 | 50 | 45 | 34 |

* The viral infection potency with no sample addition was defined 100 %.

SUGAR DERIVATIVES AND APPLICATION OF SAME

TECHNICAL FIELD

The present invention relates to a sugar derivative with a novel polysaccharide structure and the application thereof. More specifically, the invention relates to a sugar derivative of an extremely high molecular weight, with a repeat structure of a specific sugar chain unit, where a lactated, sulfated sugar is contained and a peptide or a lipid may sometimes be bound additionally, and with properties extremely differing from those of known substances belonging to the same category; chemically crosslinked products, liquid crystal gels, solubilized modified products, functionalized modified products, polyion complexes and liquid crystal slimes as individually obtained via the application of the sugar derivative; and a method for producing the sugar derivative.

BACKGROUND OF THE INVENTION

For switching from environmentally accumulated materials of petroleum chemistry to materials of biomass-derived environmentally recycling types, it has been desired to extract a novel naturally occurring polymer from microorganisms and create a functional material or formulation based on the novel naturally occurring polymer for effective applications thereof. From such standpoint, attention may satisfactorily be focused on Aphanothece sacrum as a photosynthetic freshwater blue-green alga secreting an agar-like substance at an extremely enormous amount into extracellular matrices.
[Reference 1] Kiyotaka Hanada, "Blessing of Nature, Blessings and Future of Groundwater and Spring", The Thirteenth Water Environment Academic Association Civic Seminar Lecture Proceedings, page 29 (2004)

The reference 1 reports that "it is observed that Aphanothece sacrum as a food blue-green alga has an anti-oxidation action and an anti-allergic activity". However, the reference 1 never reveals any active ingredient for these actions.
[Reference 2] Kiyotaka Hanada, Tomonobu Okamoto, Naoshige Sasada, Masateru Ono, Keiji Igoshi, Hiromasa Kobayashi, Tikako Masuoka, Yasuyuki Ito "Culture of Aphanothece sacrum (Sur.) Okada as a Blue-Green Alga Intrinsic to Japan and Examinations of its Constitutional Monosaccharides and Functionality", Annals of Researches in the Department of Agriculture, Kyushu Tokai University, No. 24, page 37 (2004).

The reference 2 reports the presence of dyes, proteins, monosaccharides, β-carotene, linolenic acid, licopin, and polysaccharides after attempts for extracting an active ingredient from Aphanothece sacrum. As the monosaccharides, glucose, mannose and xylose were detected. However, the structures of the polysaccharides were not sufficiently analyzed.

Information about Aphanothece sacrum is disclosed that processed dry products of Aphanothece sacrum never cause any fungal proliferation so that the processed dry products are never rotten (http://www.kisendou.co/shiryou.htm). Processed dry products of Aphanothece sacrum are now on market as functional health foods. This indicates the anti-bacterial property of Aphanothece sacrum.
[Reference 3] Jean-Michel Panoff, et al., "Sulfated exopolysaccharides by two unicellular strains of cyanobacteria, Synechocystis PCC 6803 and 6714", Arch. Microbiol. (1988) 150: 558-563.

The reference 3 shows only the compositions of monosaccharides in the polysaccharides derived from Synechocystis and reports a sulfated polysaccharide with N-acetylhexose, uronic acid and sulfate group. Based on the data about "sulfate residues" described in Table 1, page 561 in the reference, it is calculated that the ratio of sulfur atom in all of the elements in the sulfated polysaccharide is 1.2% by weight at maximum, while the molecular weight of the sulfated polysaccharide is not identified.

With no direct relation with the invention, alternatively, the following reference 4 for example reports that spirulan as a sulfated polysaccharide extracted from spirulina as a food blue-green alga has an anti-viral activity and the sugar components composing spirulan are neutral sugars, uronic acid, methylated sugar, sulfuric acid and the like.
[Reference 4] Toshimitsu Hayashi, et al., "Calcium Spirulan, an Inhibitor of Enveloped Virus Replication, from a Blue-Green Alga Spirulina plantensis", J. Nat. Prod. (1996), 59, 83-87.

Aphanothece sacrum is a biological species intrinsic to the Kyushu District, Japan and due to the conditions that Aphanothece sacrum is a very fragile organism with tough constraints to growth conditions and culture conditions therefor, not any satisfactory research works about Aphanothece sacrum and the agar-like substance secreted by Aphanothece sacrum have actually been done yet, except for the aforementioned several reports.

DISCLOSURE OF THE INVENTION

It is an object of the invention to extract and examine a useful component derived from Aphanothece sacrum and then reveal the chemical structure and action thereof, to consequently create a novel and useful functional material and a functional formulation. In the course of research works, the present inventors successfully extracted a sugar derivative of a novel polysaccharide structure. Through various structural analyses and research works about the functions thereof and through research works about an effective application method thereof, the inventors achieved the invention.
(First Invention)

A first aspect of the invention relates to a sugar derivative derived from Aphanothece sacrum as a freshwater blue-green alga, having a mean molecular weight of 2,000,000 or more and a repeat structure of a sugar chain unit where a sugar constituent of a hexose structure and a sugar constituent of a pentose structure are conjugated together in a linear chain or a branched chain through an α-glycoside bond or a β-glycoside bond, where 2.7 or more hydroxyl groups per 100 hydroxyl groups are sulfated or sulfur element occupies 1.5% by weight or more of all of the elements, in the sugar chain unit.

In the first aspect of the invention, the definition "derived from Aphanothece sacrum" is a part of the definitions specifying the sugar derivative as a substance but never limits the source from which the sugar derivative is obtained or the method for producing the sugar derivative.
(Second Invention)

In a second aspect of the invention, the sugar chain unit in the first aspect of the invention contains a lactated, sulfated sugar as a sugar constituent.
(Third Invention)

In a third aspect of the invention, the lactated, sulfated sugar in the second aspect of the invention is one or more selected from sulfated muramic acid and sulfated N-acetylmuramic acid.
(Fourth Invention)

In a fourth aspect of the invention, a sugar derivative in any one of the first to third aspects of the invention contains at least glucose, galactose and mannose represented by Chemical Formula 1, galactosamine represented by Chemical Formula 2, xylose and arabinose represented by Chemical Formula 3, glucuronic acid and galacturonic acid represented by Chemical Formula 4, and fucose and rhamnose represented by Chemical Formula 5, where a functional group selected from a group of functional groups at least including sulfate group, lactate group and methyl group is bound at any binding position in these sugar constituents.

[Chemical Formula 1]
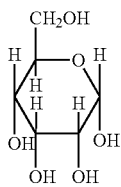

[Chemical Formula 2]
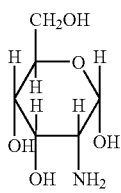

[Chemical Formula 3]
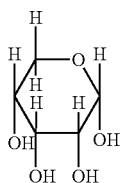

[Chemical Formula 4]
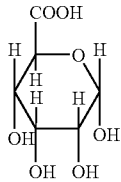

[Chemical Formula 5]
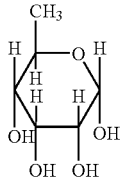

(Fifth invention)

In a fifth aspect of the invention, a part of a sugar constituent composing a sugar derivative in any one of the first to fourth aspects of the invention is additionally bound to a peptide or a lipid.

(Sixth Invention)

In a sixth aspect of the invention, a sugar derivative derived from Aphanothece sacrum as a freshwater blue-green alga has a mean molecular weight of 2,000,000 or more and contains a trisaccharide structure of a sequence represented by the Chemical Formula 6 below and all the disaccharide structures of sequences listed below in 1) to 6).

[Chemical Formula 6]
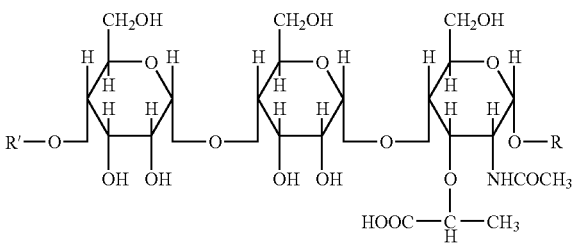

(Chemical Formula 6 represents a trisaccharide structure of hexose, hexose and N-acetylmuramic acid, where R and R' represent a sugar; and any —OH in the Chemical Formula 6 may be —$OSO_3$— or —$OCH_3$).

1) A disaccharide structure of a hexose and a pentose which is xylose or arabinose.
2) A disaccharide structure of a hexose and a deoxyhexose which is fucose or rhamnose.
3) A disaccharide structure of a pentose and a pentose.
4) A disaccharide structure of a pentose and a deoxyhexose.
5) A disaccharide structure of a hexosamine and a hexosamine.
6) A disaccharide structure of an uronic acid as glucuronic acid or galacturonic acid and a deoxyhexose.

(Seventh Invention)

In a seventh aspect of the invention, the mean molecular weight of the sugar derivative in any one of the first to sixth aspects of the invention is 20,000,000 or more.

(Eighth Invention)

In an eighth aspect of the invention, the molar ratio of main sugar constituents composing the sugar derivative in any one of the first to seventh aspects of the invention is 1.1:3.7:15.4:17.0:10.5:12.3:4.6:4.7:28.8:2.03 as the ratio of arabinose:fucose rhamnose:xylose mannose:galactose:galacturonic acid: glucuronic acid glucose:galactosamine.

(Ninth Invention)

In a ninth aspect of the invention, the sugar derivative in any one of the first to eighth aspects of the invention exhibits a solvent-absorbing property in any one or more of those listed below in (1) through (3), as measured by the tea bag method:
(1) an absorption ratio of pure water in weight ratio at 5700-fold or more;
(2) an absorption ratio of physiological saline in weight ratio at 3300-fold or more;
(3) the ratio B/A at about 0.57 or more, provided that the absorption ratio of water is defined as A and the absorption ratio of physiological saline is defined as B.

(Tenth Invention)

In a tenth aspect of the invention, the sugar derivative in any one of the first to ninth aspects of the invention exhibits such pseudo-plasticity that the viscosity of the sugar derivative is decreased as the shear velocity in an aqueous solution is increased.

(Eleventh Invention)

In an eleventh aspect of the invention, the sugar derivative in any one of the first to tenth aspects of the invention exhibits liquid crystallinity in an aqueous solution at a high concentration.

(Twelfth Invention)

In a twelfth aspect of the invention concerning the intensity of polarizing transmission light in aqueous solutions, the sugar derivative in any one of the first to eleventh aspects of the invention exhibits the increase of the intensity of the transmission light in two stages (birefringence increase) in aqueous solutions as the shear velocity is increased.
(Thirteenth Invention)

In a thirteenth aspect of the invention, the sugar derivative in any one of the first to twelfth aspects of the invention exhibits at least one of the following characteristic properties in an aqueous solution containing a metal ion.
(1) Gel formation in a dilute solution of a metal ion of the group 3 and the group 13 at $10^{-3}$ M concentration.
(2) Gel formation in a solution of a metal ion selected from the rare earth metal ion group including at least ytterbium ion $Yb^{3+}$, even when the solution is at any of alkalinity, neutrality or acidity.
(Fourteenth Invention)

A fourteen aspect of the invention relates to a chemically crosslinked sugar derivative obtained via a reaction of a functional group of the sugar derivative in any one of the first to thirteen aspects of the invention with a polyfunctional compound for crosslinking.
(Fifteenth Invention)

A fifteen invention is a sugar derivative-modified product obtained by modifying a functional group of the sugar derivative in any one of the first to thirteenth aspects of the invention with a compound for solubilization or functionalization or with a dye compound.
(Sixteenth Invention)

A sixteen aspect of the invention relates to a polyion complex as a complex of the sugar derivative in any one of the first to thirteenth aspects of the invention with a polycation compound.
(Seventeenth Invention)

A seventeenth aspect of the invention relates to a liquid crystal gel as a polysaccharide-metal ion hybrid liquid crystal gel, obtained by putting an aqueous solution of a high concentration of the sugar derivative in any one of the first to thirteenth aspects of the invention or of the chemically crosslinked sugar derivative in the fourteenth aspect of the invention in contact with a polyvalent metal ion.
(Eighteenth Invention)

In an eighteenth aspect of the invention, the polyvalent metal ion in the seventeenth aspect of the invention is one or more selected from ions of individual metals of Al, Se, Ti, V, Cr, Fe, Ga, Sr, Y, Zr, Nb, Ru, Rh, Pd, Cd, In, Ba, La, Hf, Ta, W, Re, Os, Ir, Hg, Pr, Bi, Ce, Nd, Sm, Eu, Gd, Tb, Dy, Ho, Er, Tm, Yb, Lu and U.
(Nineteenth Invention)

A nineteenth aspect of the invention relates to a liquid crystal slime as a polysaccharide liquid crystal slime, as obtained by putting an aqueous solution of a high concentration of the sugar derivative in any one of the first to thirteenth aspects of the invention in contact with a metal ion selected from a group including at least calcium ion $Ca^{2+}$.
(Twentieth Invention)

A twentieth aspect of the invention relates to a sugar derivative formulation containing the sugar derivative in any one of the first to thirteenth aspects of the invention as the active ingredient and having at least one of the following applications.
(1) An agent for water absorption, water retention and moisture retention.
(2) An anti-bacterial agent.
(3) An anti-viral agent.
(4) An anti-cancer agent.
(5) A health promotion agent for use in foods.
(6) A thickener and stabilizer for foods
(7) A metal recovery agent.
(8) A caking and adhesive agent.
(9) A soil modifier.
(10) An infection preventive agent.
(Twenty-First Invention)

A twenty-first aspect of the invention relates to a method for producing a sugar derivative comprising extracting the sugar derivative in any one of the first to thirteenth aspects of the invention from a freshwater blue-green alga Aphanothece sacrum and purifying the sugar derivative if necessary.

BRIEF DESCRIPTION OF THE DRAWINGS

FIG. 2 depicts a photograph of the sugar derivative in a fibrous state.
FIG. 5 depicts an ultraviolet/visible spectrum of a sample.
FIG. 10 shows the gelation of the polysaccharide.
FIGS. 21 and 22 show the data by which the sequence of sugars composing the polysaccharide is identified.
FIG. 24 is a table of anti-viral properties of the polysaccharide.
FIG. 25 is a table of anti-viral properties of the polysaccharide.

Figure 1:
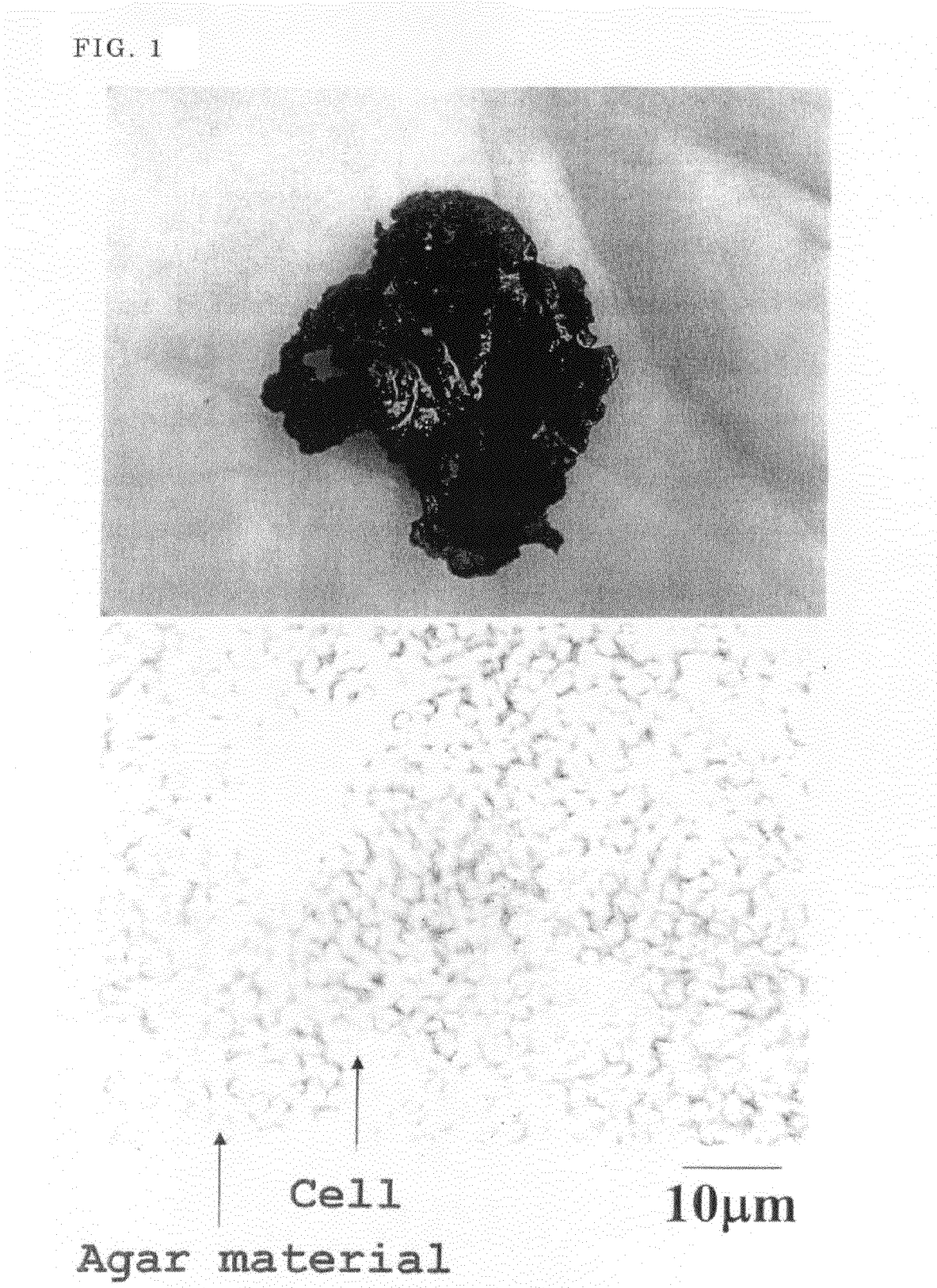
FIG. 1 depicts a photograph of Aphanothece sacrum.

BEST MODE FOR CARRYING OUT THE INVENTION (1) Providing a useful sugar derivative with a novel polysaccharide structure as derived from Aphanothece sacrum and as defined in the first to sixth aspects of the invention.

(2) The sugar derivative of the invention has a molecular weight of at least 2,000,000 or more, preferably 20,000,000 or more. A naturally occurring sulfated polysaccharide with such an ultra-super molecular weight as more than 8,000,000 was first found.

(3) The sugar derivative of the invention contains a lactated, sulfated sugar, such as sulfated muramic acid and sulfated N-acetylmuramic acid as a sugar constituent in the repeat structure. Lactated sugars such as muramic acid and N-acetylmuramic acid as sugar constituents in the peptide glycan in bacterial cell walls have been verified conventionally. However, no saccharide containing a lactated, sulfated sugar has yet been reported. In other words, the sugar derivative contains a lactated sugar and a sulfated sugar, so that the acidity around the sugar chain can be retained high. Since lactic acid is eliminated at room temperature in an aqueous acidic solution of the sugar derivative, then, lactic acid is released with gastric acid when the sugar derivative is orally given, so the sugar derivative will exhibit an action for soothing intestinal disorders.

(4) The sugar derivative of the invention contains at least hexose and pentose represented by the Chemical Formulas 1 through 5, where functional groups such as sulfate group, lactate group and methyl group are bound to an appropriate binding position in these sugar constituents. Further, a part of the sugar constituents composing the sugar derivative is bound to a peptide or a lipid.

(5) As described in the sixth aspect of the invention, the sugar derivative of the invention includes a trisaccharide structure with the sequence represented by the Chemical Formula 6 and all of the disaccharide structures with the sequences listed in 1) through 6). The sugar derivative is decomposed with an acid for FT-MS. Consequently, it was found that the trisaccharide constituent and the disaccharide constituents were dissociated together.

(6) Furthermore, the sugar derivative of the invention is at the following molar ratio of the main sugar constituents composing the sugar derivative. That is, arabinose 1.1:fucose 3.7:rhamnose 15.4:xylose 17.0:mannose 10.5:galactose 12.3:galacturonic acid 4.6:glucuronic acid 4.7: glucose 28.8: galactosamine 2.03. The sugar constituents identified as described above occupy 94% of the whole sugar derivative. It is understood that sugars such as muramic acid may be contained in the remaining 6%.

(7) Since the sugar derivative of the invention exhibits very excellent absorption properties of solvents, such as absorption ratios of pure water in weight ratio at 5700 fold and of physiological saline at 3300 fold, according to the tea bag method, the sugar derivative is extremely useful as an agent for water absorption, water retention and moisture retention. The "tea bag method" is a method for measuring the absorption ratio of solvents as described below.

Specifically, a solution of the sugar derivative in pure water or physiological saline as a solvent is placed in a bag made of kitchen paper. After the bag is immersed in a beaker containing a large volume of a solvent of the same type and left to stand for 2 hours, the bag is drawn up and hung. The hanging state is retained until no liquid droplet is fallen down from the bag (in about 5 hours, generally). Subsequently, the solution in the bag is recovered, to determine the weight Ws of 10 mL of the solution and the weight W of the sugar derivative contained therein (W can be determined by weighing the residue after thoroughly drying the solution in vacuum) and then calculate Ws/W to determine the absorption ratio of the solvent.

(8) It was verified that the sugar derivative of the invention exhibited the pseudo-plasticity. Like known gum xantham, for example, the sugar derivative is useful as an additive for thickening mayonnaise and the like.

(9) The sugar derivative of the invention exhibits liquid crystallinity never found in conventional sulfated polysaccharides naturally occurring and also exhibits the increase of birefringence in two stages as never found in any report about conventional polysaccharides; the sugar derivative forms a gel in any liquid property of alkalinity, neutrality and acidity in a metal ion solution and also forms a liquid crystal gel of a novel concept, which is a polysaccharide-metal ion hybrid liquid crystal gel; and the sugar derivative further forms a polysaccharide liquid crystal slime via a reaction with calcium ion and the like. As described above, the sugar derivative of the invention exhibits various properties very unique. The liquid crystal gel is more specifically described below in (14). By utilizing these characteristic properties, the sugar derivative may be applicable to uses including for example polarization lenses, photo-trapping agents, photo-scattering agents, flow rate sensors, play toys, actuators, and adhesives.

(10) Since the anti-oxidation action and anti-allergic activity of Aphanothece sacrum from which the sugar derivative of the invention is derived is reported and it is known that Aphanothece sacrum is anti-bacterial and spirulan as a sulfated polysaccharide is anti-bacterial, it can surely be confirmed that the sugar derivative of the invention has excellent anti-bacterial activity and anti-viral activity. Furthermore, it can be expected that the sugar derivative may have an anti-oxidant action and anti-allergic action. Thus, the sugar derivative of the invention can be used as an active ingredient for anti-bacterial agents, anti-viral/anti-cancer agents, health promotion agents for use in foods, and thickeners and stabilizers for foods. More specifically, various applications described above in the twentieth invention can be listed. These applications include for example medical supplies such as mask and white coat, sanitary products such as diaper and napkin, filters for air conditioner and air cleaner, water retention agents for soil for preventing infections, feed additives for preventing infections, and food additives for preventing infections.

(11) The inventors obtained a chemically crosslinked sugar derivative via a reaction of a functional group of the sugar derivative with a polyfunctional compound for cross linking. The functional group for crosslinking includes for example the hydroxyl group, amino group, and carboxyl group of the sugar derivative. The polyfunctional compound includes for example polyfunctional isocyanates, polyfunctional epoxy compounds, polyfunctional carboxylic acids, polyfunctional carboxylate derivatives, polyfunctional halides and polyfunctional vinyl compounds. The crosslinking density can be controlled to about 0.001 mol/% to 15 mol/% of the sugar constituents. The chemically crosslinked sugar derivative of the invention turns a gel when the sugar derivative absorbs a liquid such as water, which is plasticized into rubber by heating or by adding a plasticizer.

(12) A functional group of the sugar derivative of the invention can be modified with a compound for solubilization or functionalization or can be modified with a dye compound.

For example, the sugar derivative of the invention was dissolved in an anhydrous organic solvent such as DMSO for a reaction with acetic anhydride or acetic chloride, so that an acetylated sugar derivative could be prepared, where the hydroxyl group of the sugar derivative was acetylated. In case of acetylation, the formation of hydrogen bond in the sugar derivative is suppressed, so that the solubility thereof in a hydrophilic solvent such as water can be increased. Similarly, the sugar derivative can be solubilized or functionalized, using other types of carboxylic anhydride or carboxylic chloride.

In addition to those described above, the method for solubilizing or functionalizing the sugar derivative includes hydroxypropylation, hydroxyethylation, carboxymethylation, sulfation, sulfonation, preparation as sulfur derivatives, tosylation, mesylation, methylation, chloromethylation, formylation, sulfination, phosphorylation, phosphonation, phosphination, preparation as phosphorous derivatives, boration, boronation, preparation as boron derivatives, silication, preparation as silyl derivatives, nitration, nitrosylation, nitrylation, halogenation, hydroxylation, epoxylation, primary to quaternary amination, azomethination, azonation, azoxylation, diazotization, azidation, pyridylation, pyrazylation, triazination, pyrrolation, piperidination, pyrimidination, pyrrolidination, purination, toluidination, styrylation, phenylation, phenoxylation, benzylation, benzoylation, benzyloxylation, halogenophenylation, halogenophenoxylation, halogenobenzylation, halogenobenzoylation, halogenobenzyloxylation, naphthylation, anthrylation, phenanthrylation, preparation as derivatives including aromatic compounds, alkylation, alkenylation, alkynylation, alkoxylation, alkenoxylation, alkynoxylation, cycloalkylation, cycloalkenylation, cycloalkynylation, cycloalkoxylation, cycloalkenoxylation, cycloalkynoxylation, halogenoalkylation, halogenoalkenylation, halogenoalkynylation, halogenoalkoxylation, halogenoalkenoxylation, halogenoalkynoxylation, crown etherification, lactation, glycolation, cholesterylation, glycylation, lipidation, preparation as amino acid derivatives, saccharification, preparation as nucleic acid derivatives, terpenylation, preparation as alkaloids, preparation as flavonoids, and glycosidation. Additionally, the aforementioned individual derivatives may also be prepared as heavy hydrogen derivatives, derivatives containing $^{13}C$, and derivatives containing radioactive isotopes.

For modifying the sugar derivative with a dye compound, a method for chemically binding the hydroxyl group, amino group or carboxyl group of the sugar derivative with an appropriate chromogen as well as a method for physically binding such group using an electrostatic interaction is exemplified. Via the modification of the sugar derivative with a dye, for example, advantages such as an additional value of chromogenicity, application to color filters, applications to highly dispersible pigments, and application to water-soluble dyes can be obtained.

(13) As described below in Examples, a polyion complex as a complex of the sugar derivative of the invention with a polycation compound could be obtained. The recovery of such polyion complex can bring about advantages for example salt absorbing agents, substance carriers, agents for releasing substances in a sustained mode, neutralizing agents and buffers.

(14) The polysaccharide-metal ion hybrid liquid crystal gel described above in (9) may possibly be formed not only with the sugar derivative of the invention but also with the chemically crosslinked sugar derivative of the invention via the contact with various polyvalent metal ions. The polyvalent metal ion includes at least one of ions of individual metals of Al, Se, Ti, V, Cr, Fe, Ga, Sr, Y, Zr, Nb, Ru, Rh, Pd, Cd, In, Ba, La, Hf, Ta, W, Re, Os, Ir, Hg, Pr, Bi, Ce, Nd, Sm, Eu, Gd, Tb, Dy, Ho, Er, Tm, Yb, Lu and U.

(15) As described below in Examples, it was revealed that the viscosity of an aqueous solution of the sugar derivative of the invention hardly decreased even when an acidic substance such as ascorbic acid was added. Therefore, the properties thereof such as thickening effect as an additive were advantageously never influenced by other additives.

EXAMPLES

Examples of the invention are now described below. The technical scope of the invention is never limited by the following Examples.

First Example Group

Example 1

Extraction of Sugar Derivative

In the upper column, FIG. 1 shows a full-scale photograph of a mass of Aphanothece sacrum, while in the lower column, a photograph of Aphanothece sacrum with an optical microscope is shown.

First, fresh Aphanothece sacrum of an appropriate volume was frozen, and then thawed and washed in water, to remove water-soluble dyes; subsequently, fat-soluble dyes were removed from the resulting Aphanothece sacrum under overnight agitation in ethanol. Aphanothece sacrum from which the dyes were removed in such manner were separated from ethanol, heated in an aqueous 0.05 N sodium hydroxide solution at 40° C. for solubilization over about 2 hours.

An aqueous solution of the sugar derivative extracted by the aforementioned procedures was filtered through a gauze cloth, and the resulting filtrate was placed in a dialysis membrane of a fractionation molecular weight of 8,000, for dialysis against distilled water. Until the outer dialysis solution reached pH 8.0 to 9.0, the dialysis was continued while distilled water was exchanged with fresh one every morning and night.

After completion of the dialysis, the aqueous sugar derivative solution was concentrated with an evaporator, and the resulting concentrate was poured into 100% isopropanol under agitation, to recover the sugar derivative in a fibrous state as shown in FIG. 2. FIG. 2 shows in the upper column a photograph of the fibrous material immediately after precipitation, while the lower column shows a photograph thereof with an optical microscope. It is understood that 1) an abnormally large molecular weight of the sugar derivative, 2) the presence of N-acetylhexose inducing a strong inter-molecular chain interaction, and 3) the presence of sulfate group as a functional group fairly dissolvable in water but absolutely never dissolvable in alcohol have some relations with such phenomenon of fibrous preparation.

Example 2

Infrared Absorption Spectrum of Sugar Derivative

Figure 3:
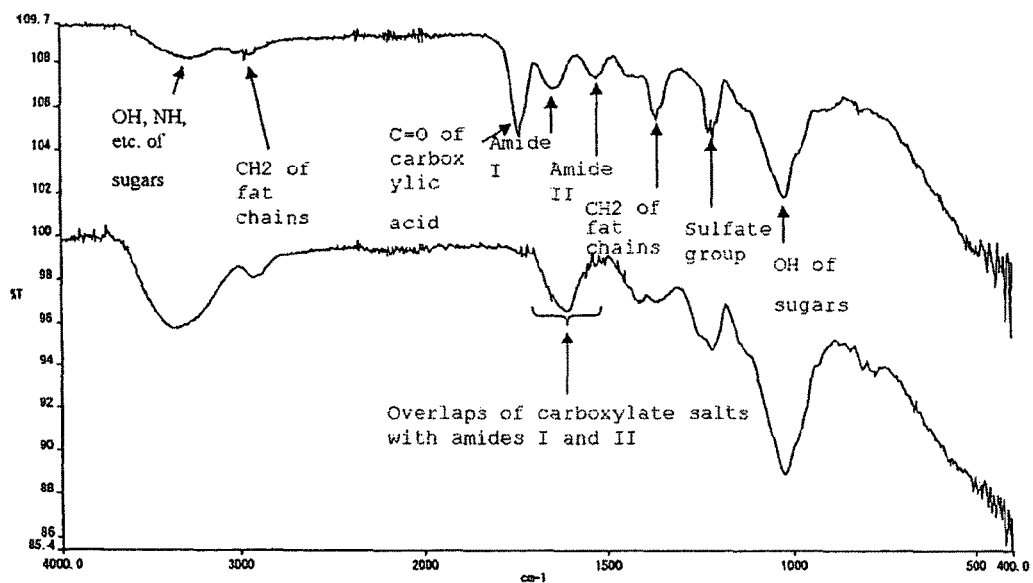
FIG. 3 depicts an infrared absorption spectrum of a sugar derivative.

The infrared absorption spectrum of the fibrous sugar derivative obtained by the treatment of the aqueous sugar derivative solution (pH 8.5) after completion of the dialysis was measured. Consequently, a peak of carbonyl group in the amides and the carboxylate ion was observed around 1650 $cm^{-1}$ as shown in the lower spectrum chart in FIG. 3. Using hydrochloric acid, the aqueous sugar derivative solution was adjusted to pH 2.5, for protonation. Then, the resulting sugar derivative solution was measured again for infrared absorption spectrum. As shown in the upper spectrum chart in FIG. 3, peaks of carbonyl groups derived from the amides and a peak of carbonyl group derived from the carboxylic acid were clearly observed. Additionally, a peak of sulfate ion was observed together with peaks of hydroxyl group around 3300 $cm^{-1}$ and 1000 $cm^{-1}$, which are characteristic to sugars.

Example 3

Recovery of Sugar Derivative without Peptide

The sugar derivatives above in Examples 1 and 2 were bound with peptides. By carrying out the thermal treatment in the aqueous sodium hydroxide solution at 120° C., a sugar derivative differing from the sugar derivative described above in that no peptide was bound thereto was also recovered. For convenience, the sugar derivative bound with a peptide is referred to as "polysaccharide peptide" while the sugar derivative with no peptide bound thereto is simply referred to as "polysaccharide" hereinbelow.

Example 4

Elemental Analysis of Polysaccharide

A sample of the polysaccharide was subjected to an elemental analysis according to a routine method. Consequently, it was found that sulfur element occupied 2.13% of the total weight of the sample. Additionally, other several samples of the polysaccharide were similarly analyzed. At minimum, sulfur element was contained at about 1.5% of the total sample weight. Some of the samples were at a sulfur element content of 2.5% or more of the total sample weight at maximum. When calculated provided that no sulfur element was contained except the sulfur element in the sulfate group, the molar ratio of sulfate group per one monosaccharide was 0.1196 in case that the sulfur element occupied 2.13% of the total sample weight. From the standpoints that 3 hydroxyl groups are generally contained in one monosaccharide and that hydroxyl group or amino group is sulfated (amino group may sometimes exist in place of hydroxyl group), it was calculated that the number of sulfate groups per one hydroxyl group was a numerical figure ⅓-fold that of the molar ratio, namely "0.03988". In other words, hydroxyl groups in the number of about 3.9 were sulfated per 100 hydroxyl groups. Based on the same calculation, it is calculated that hydroxyl groups in the number of about 2.7 are sulfated per 100 hydroxyl groups in case that sulfur element was at 1.5% of the total sample weight.

Example 5

Molecular Weight

Figure 13:
FIG. 13 is a photograph of the molecular chains of the polysaccharide with an electron microscope.

An aqueous dilute solution of the polysaccharide was diluted with isopropanol, and was then dropwise added onto a carbon-coated copper grid for drying. FIG. 13 shows a photograph of the sample with a transmission type electron microscope.

Because the sample was dried from the dilute solution, the imaged polysaccharide may be in a form of a single molecule chain. The length of the molecular chain was estimated to be at least 5 μm or more, based on the 100-nm size bar shown in the lower part of the figure. Provided that the length of one monosaccharide with a molecular weight of 180 on assumption is 0.4 nm, the molecular weight thereof would be 2,250,000 because the molecular chain is 12,500-mers. On the photograph with a transmission type electron microscope, a great number of molecular chains of far longer lengths were also observed.

Example 6

NMR Spectrum

Figure 4:
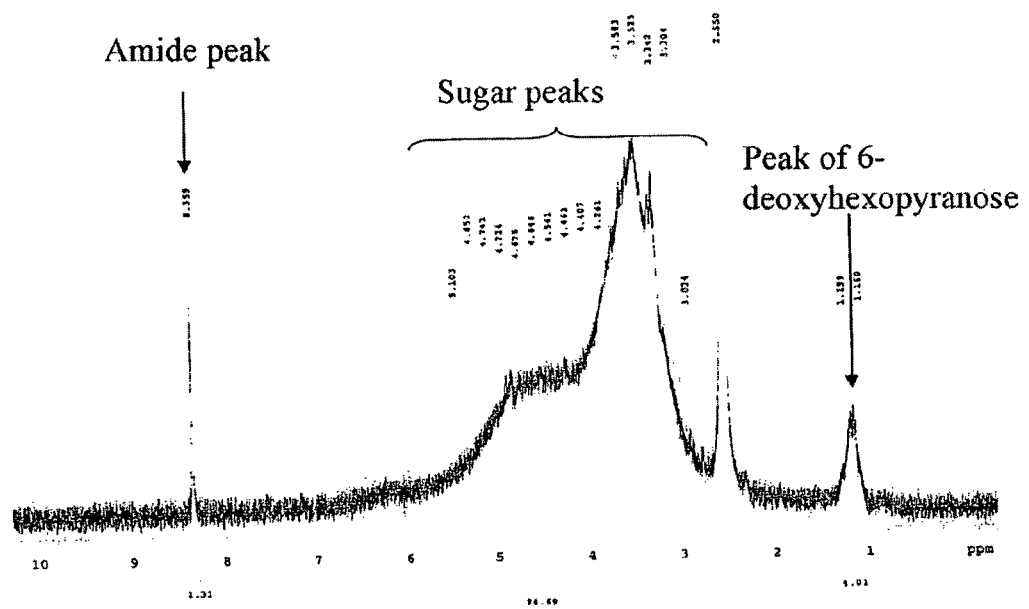
FIG. 4 depicts an NMR spectrum of a sample.

The polysaccharide was hydrolyzed with trifluoroacetic acid for $^1$H NMR spectroscopy. As shown in FIG. 4, proton peaks derived from amide, sugars and 6-deoxysugar were observed. A similar $^1$H NMR spectrum was also obtained for the polysaccharide peptide.

Example 7

Infrared/Visible Spectrum

Infrared/visible spectra of the polysaccharide and the polysaccharide peptide were measured. As shown in FIG. 5, none of the absorption specific to peptides around 240 to 280 nm was observed in case of the polysaccharide, while the absorption was observed in case of the polysaccharide peptide. In any of the cases, alternatively, sugar-specific absorption was observed at 240 nm or less.

Example 8

ESI-MS Spectrum

Figure 6:
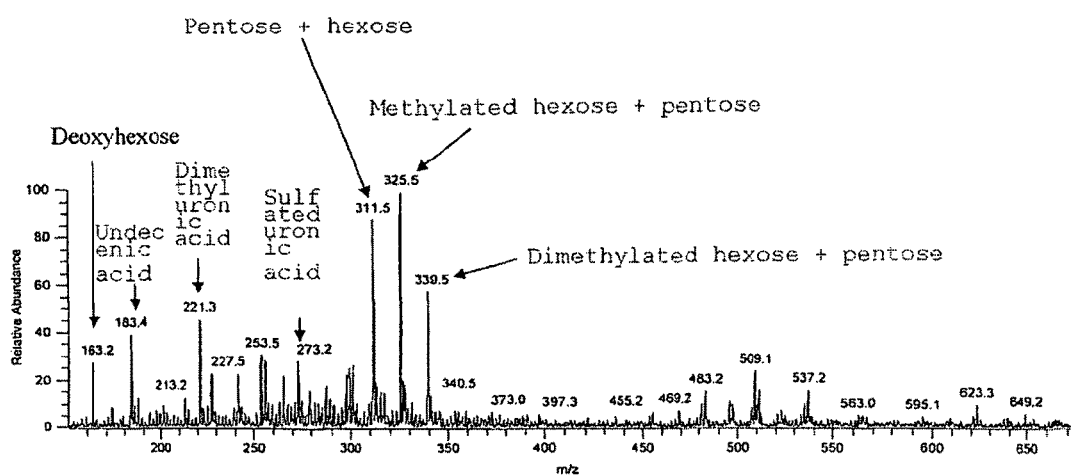
FIG. 6 depicts an ESI-MS spectrum of an acid decomposition product of a sample.

The polysaccharide was decomposed with an acid, for measuring the ESI-MS spectrum, so that the results shown in FIG. 6 were obtained. Based on the molecular weights of monosaccharides and disaccharides, the presence of hexose, pentose, deoxyhexose, N-acetylhexose, sulfated uronic acid and uronic acid was confirmed.

Example 9

Speculation of Polysaccharide Structure

Based on the results of the aforementioned various analyses, the chemical structures of the polysaccharide and the polysaccharide peptide were determined, as described above.

Example 10

Visco-Elasticity Test

Figure 7:
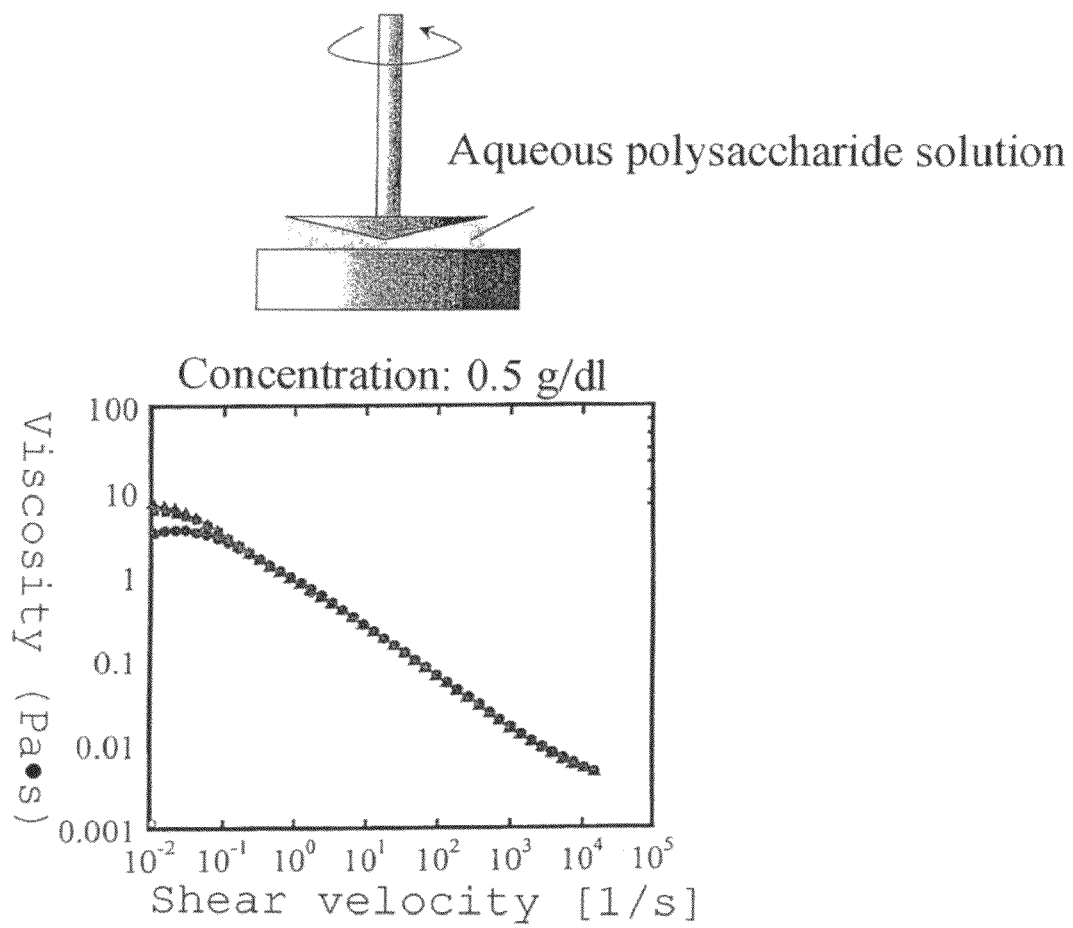
FIG. 7 shows the method for testing visco-elasticity and the test results.

Using a rotation viscosity system shown in the upper part of FIG. 7, a visco-elasticity test of the polysaccharide was done. With the rotation viscosity system, an aqueous polysaccharide solution at an appropriate concentration was placed in an appropriate container to a disk shape of a 1-mm thickness and a 20-mm diameter; under rotation of the aqueous solution at various shear velocities, the rotation torque was measured as the viscosity. An aqueous polysaccharide solution at a concentration of 0.5 g/dl was measured in such manner triplicately in total. The results are shown in the lower part of FIG. 7.

Example 11

Shear Stress-Induced Birefringence

Figure 8:
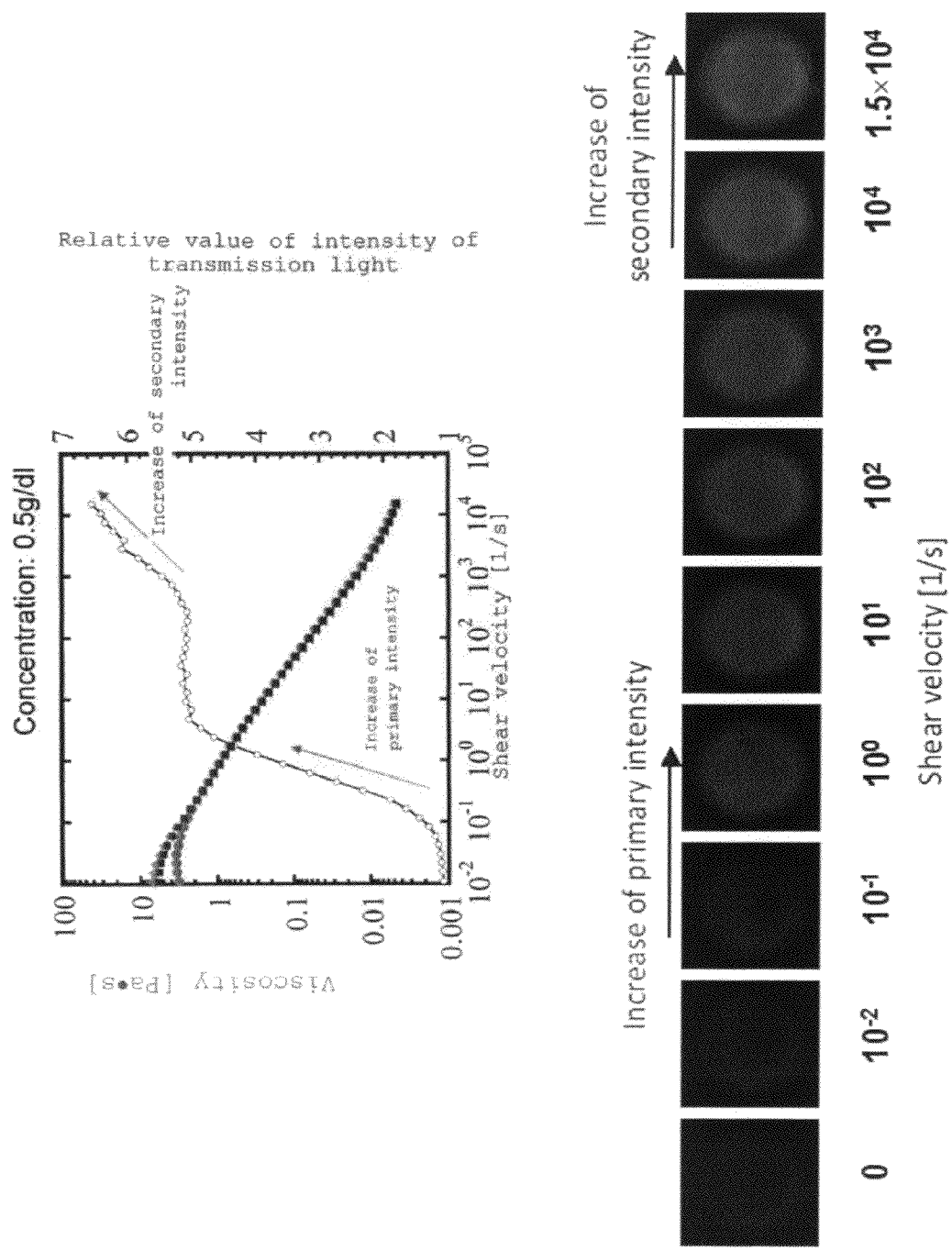
FIG. 8 shows shear stress-induced birefringence of a sample.

Placing an aqueous polysaccharide solution at a concentration of 0.5 g/dl between crossed polarizers, the intensity of light transmitting through the aqueous solution was measured when a shear stress was loaded to the aqueous solution. The results of the measurement are shown in the upper part of FIG. 8, while the lower part of FIG. 8 shows a photograph showing the change of the intensity of transmission light as the shear velocity increased.

Consequently, it was indicated that the transmission light intensity was increased in two stages as the shear velocity increased. The increase of the transmission light intensity indicates the increase of the birefringence of the aqueous solution. Further, the increase of birefringence indicates the orientation of the molecular chains in the aqueous solution along one direction. Primary orientation of molecules is derived from the liquid crystal phase of the molecular chains, while secondary orientation of molecules shows that the lineality of the molecular chains themselves is raised. No other reports exist, telling about any such polysaccharides with the increase of birefringence in two stages as described above.

Example 12

Liquid Crystallinity of Polysaccharides at High Concentration States

Figure 9:
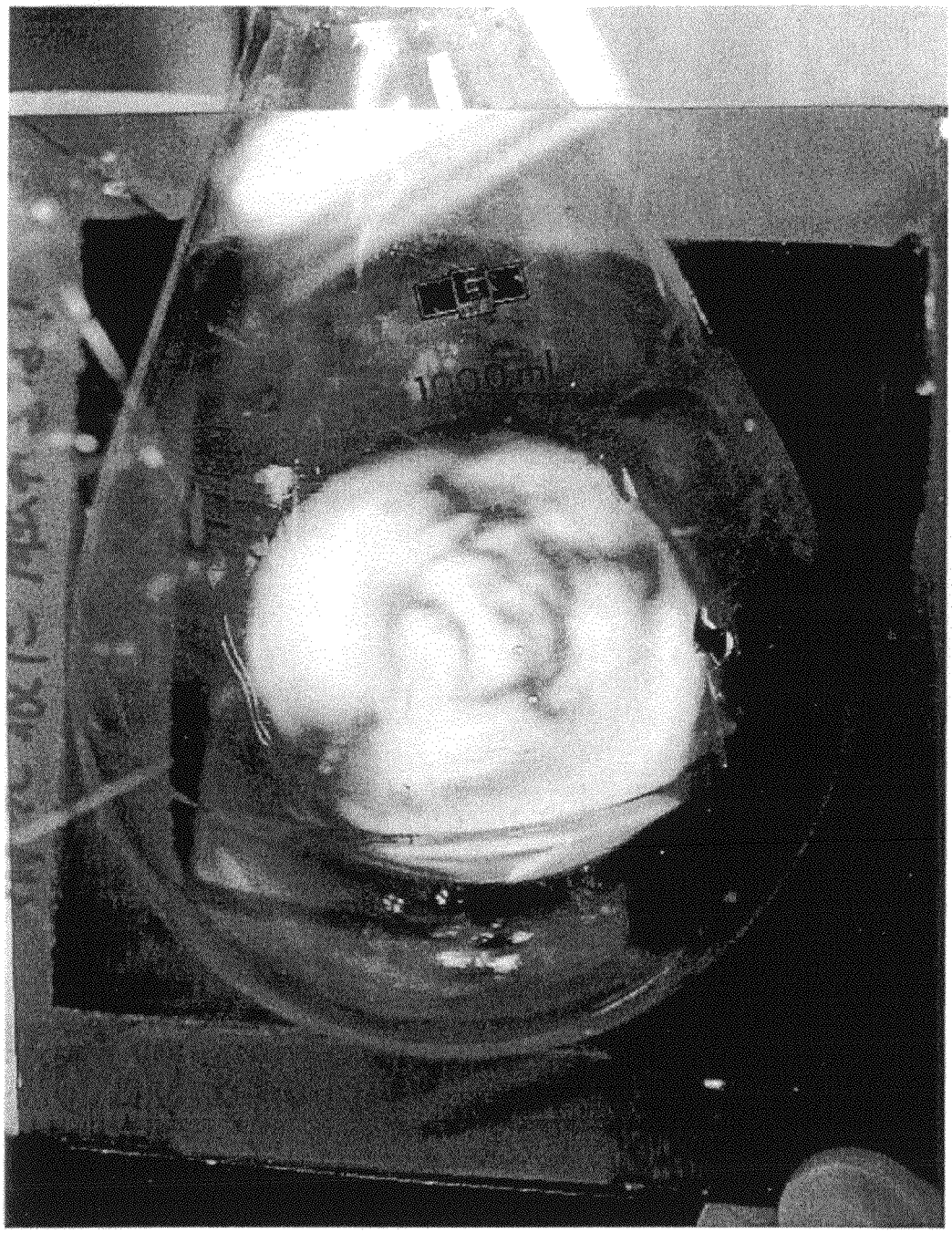
FIG. 9 shows a polarization photograph of the polysaccharide at a liquid crystal state.

In case that the concentration of an aqueous polysaccharide solution is higher than 0.5 g/dl, a liquid crystal phase emerges without any shear stress. The photograph in FIG. 9 shows that an aqueous polysaccharide solution at a concentration larger than 0.5 g/dl is placed under crossed polarizers. The photograph indicates that the aqueous solution exhibits strong birefringence and that the aqueous solution at the spontaneous state exhibits a liquid crystal phase. As such substance, schizophyllan as a neutral polysaccharide is listed. However, the polysaccharide exhibiting liquid crystallinity was the first naturally occurring sulfated polysaccharide.

Example 13

Polysaccharide Gelation

When aqueous solutions of the polysaccharide and the polysaccharide peptide are dropwise added to an aqueous metal ion solution, the resulting aqueous solutions instantly self-organize into a gel. This is due to the interaction between sugar anions and the cation of the metal ion. Alginic acid is famous as such known naturally occurring polysaccharide.

FIG. 10 shows photographs of gelation statuses of alginic acid and the polysaccharide of the invention in the presence of $10^{-2}$ M $Yb^{3+}$. The photograph in the upper part of FIG. 10 shows the gelation statuses at neutrality or alkalinity, where the left beaker contains alginic acid and the right beaker contains the polysaccharide. In both of the beakers, gel formation can be observed. The photograph in the lower part of FIG. 10 shows the gelation statuses at acidity, where the left beaker contains alginic acid and the right beaker contains the polysaccharide. Gel formation can be observed in case of the polysaccharide alone.

As described above, such polysaccharide forming a gel at any liquid properties from acidity to alkalinity was first found presently. The reason is the presence of abundant sulfate group in addition of carboxylic acid and the presence of an appropriate amount of N-acetylhexose (scarcely soluble in water). Even in the presence of a rare earth metal ion other than $Yb^{3+}$ ion, the same phenomenon could be observed, although the figures are not shown because of complications.

The metal ion species with which aqueous polysaccharide solutions form gel includes $Al^{3+}$, $Sc^{3+}$, $Cr^{3+}$, $Fe^{3+}$, $Y^{3+}$, $La^{3+}$, $Ce^{3+}$, $Pr^{3+}$, $Nd^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $In^{3+}$, $Pb^{2+}$, and $Lu^{3+}$, as verified. At a $10^{-3}$ M concentration of such metal ion, gel formation can occur, possibly because of the abnormally large molecular weight of the polysaccharide, the high density of the electrical charge and the ready tanglement of the molecular chains.

Example 14

Formation of Liquid Crystal Gel and Liquid Crystal

Figure 11:
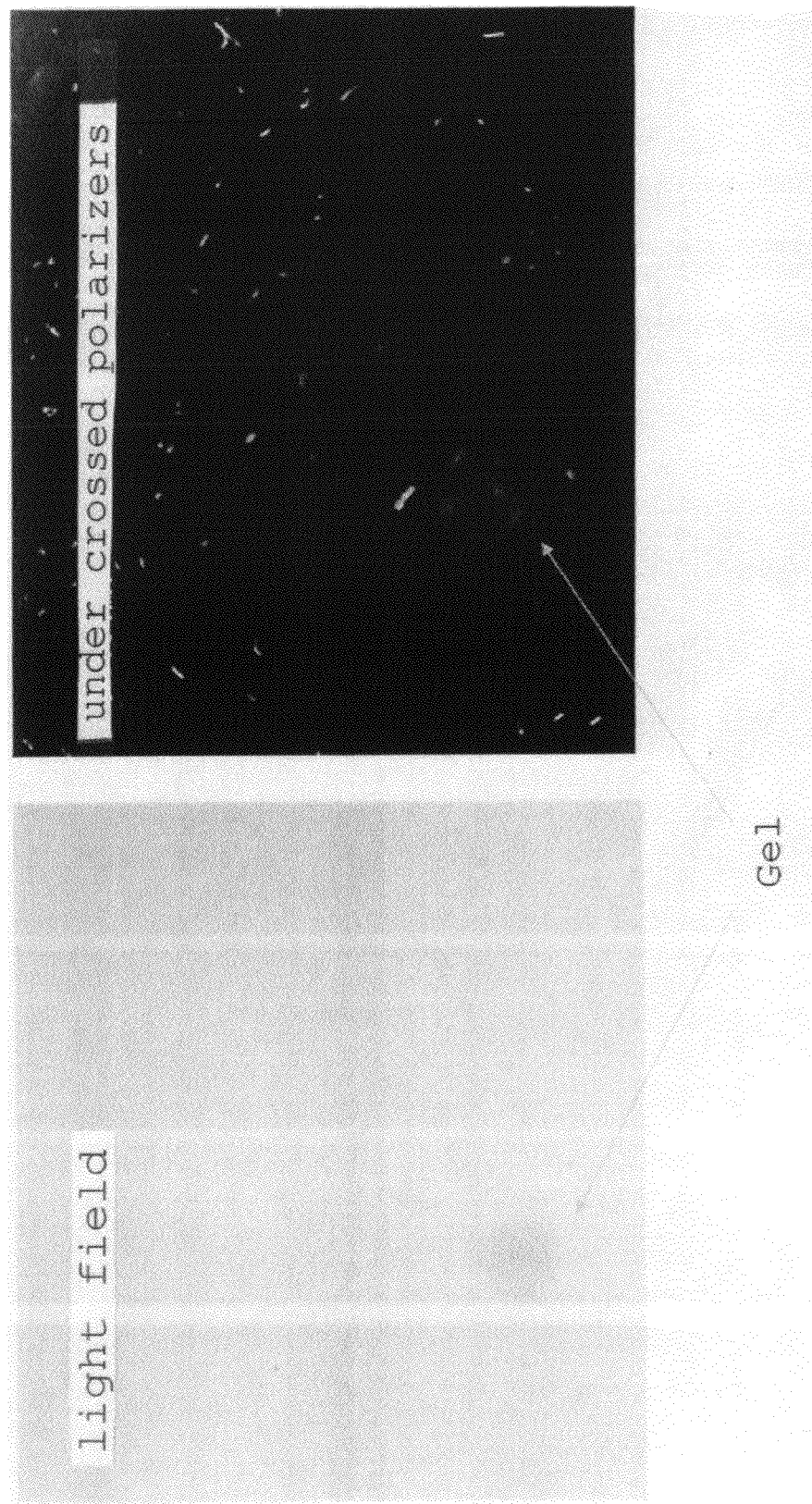
FIG. 11 depicts the formation of a liquid crystal gel from the polysaccharide.

When the polysaccharide of the invention at a concentration higher than 0.5 g/dl is dropwise added to an aqueous metal ion solution (in a $10^{-2}$ M aqueous solution of $Yb^{3+}$ ion), the polysaccharide forms a gel, as shown on the left side of FIG. 11. When light transmits through the aqueous solution under crossed polarizers, an image shown in the photograph on the right side of FIG. 11 can be obtained. A liquid crystal gel as such polysaccharide-metal hybrid has never been reported so far.

Figure 12:
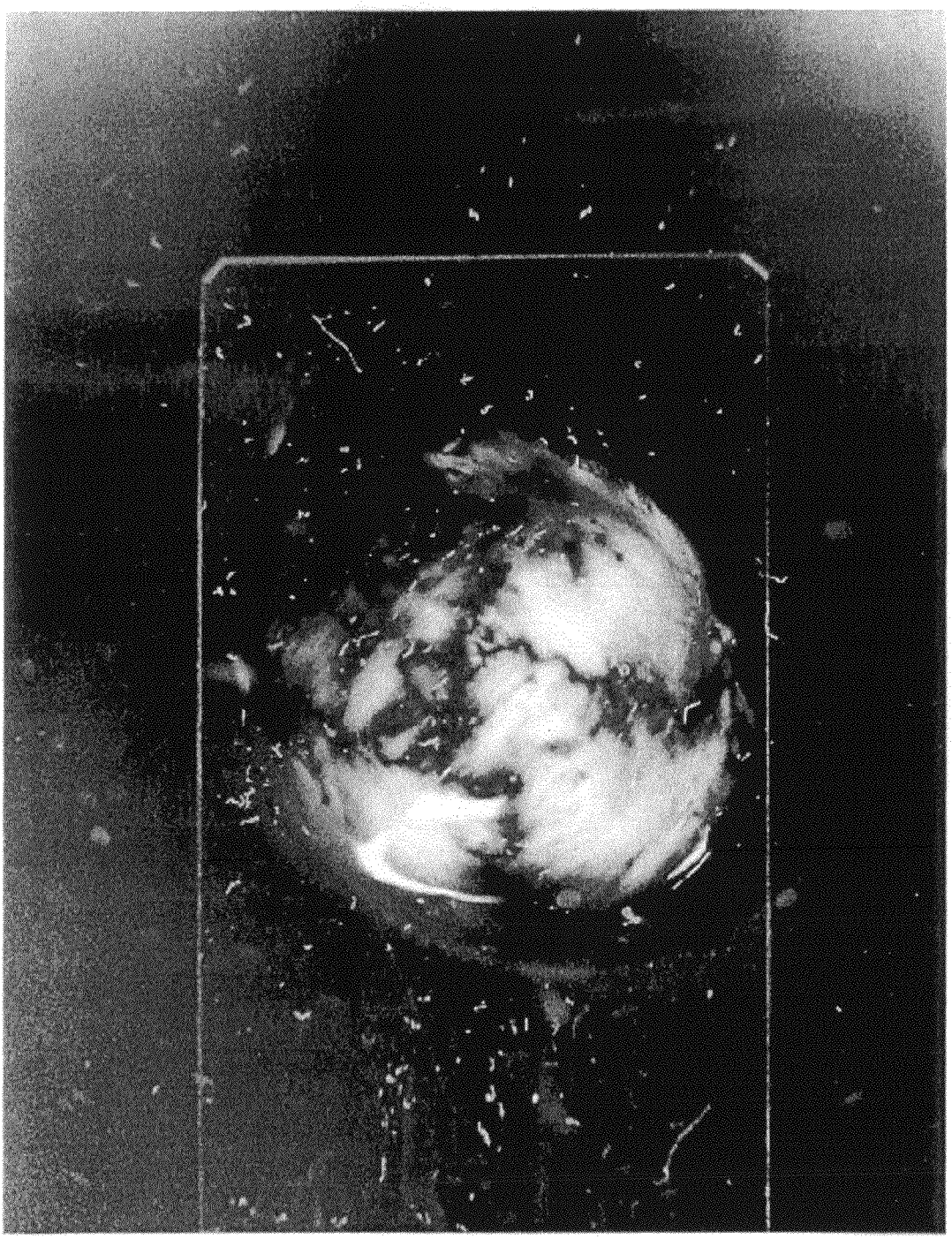
FIG. 12 depicts the formation of a liquid crystal slime from the polysaccharide.

When an aqueous polysaccharide solution at a concentration higher than 0.5 g/dl is mixed with an aqueous calcium ion solution, the aqueous polysaccharide solution turns slime (the photograph in FIG. 12). The term "slime" means a property deformable and spreadable more or less on a plane plate but never flowable. Unlike gel, additionally, slime is never cut with a cutter or is broken even when attempts are made to break slime. Such liquid crystal slime is a concept never found in any reports.

Second Example Group

Example 15

Molecular Weight Analysis of Polysaccharide Obtained by Another Extraction Method The molecular weight analysis of a polysaccharide obtained by an extraction method differing from that in Example 1 was carried out. Specifically, a water mixture of an appropriate amount of Aphanothece sacrum was treated in an autoclave at 135° C. for 30 minutes, to obtain an aqueous solution more or less turbid. The turbidity was removed with a centrifuge at a rotation number of 50,000 for 30 minutes, to obtain an aqueous transparent solution with viscosity. The aqueous solution was concentrated under reduced pressure, and poured into isopropanol, to obtain a fibrous polysaccharide. The fibrous polysaccharide was purified and analyzed in the same manner as in Example 1 or 2. Consequently, it was found that the polysaccharide had the same functional groups as in the case of the extraction method in Example 1.

Figure 14:
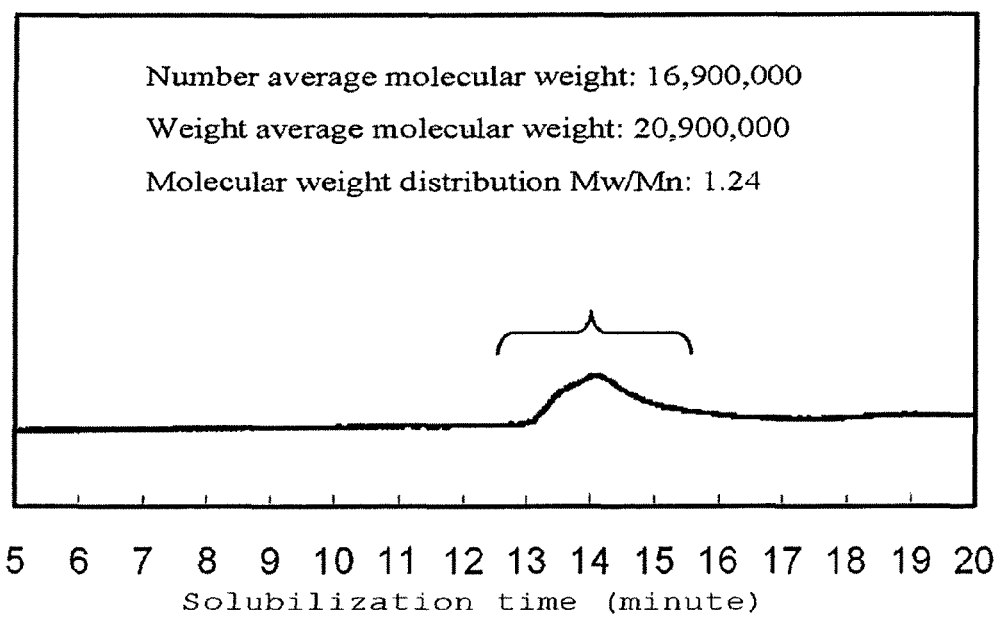
FIG. 14 shows the molecular weight data of the polysaccharide.

The polysaccharide obtained in the Example was dissolved in an aqueous 0.1M sodium nitrate solution, to measure the molecular weight thereof with an aqueous column. The results are shown in FIG. 14, indicating that the molecular weight of the polysaccharide is extremely large, with 16.9 MDa as the number average molecular weight, 20.9 MDa as the weight average molecular weight and 1.24 as the molecular weight distribution. In other words, it was estimated that the polysaccharide would have a molecular weight of about 20 MDa. According to the same analysis of sulfation degree as described above, the sulfation degree per unit monosaccharide of the polysaccharide was 100% (300% at maximum).

Example 16

Verification of Lactation

Figure 15:
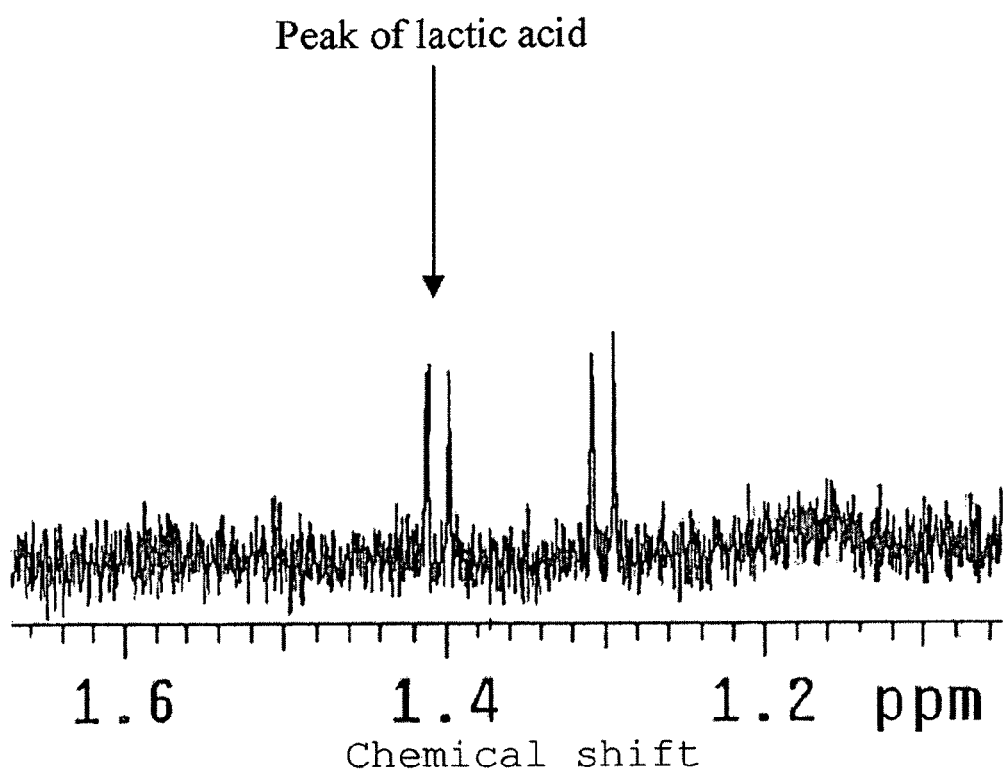
FIG. 15 shows the evidence for the lactation of the polysaccharide.

An aqueous solution of the polysaccharide obtained in Example 15 was protonated by a treatment using a protonated cation exchange resin, which was then concentrated as it was with an evaporator, for partial hydrolysis. When methanol is added to the concentrate solution, precipitates emerge. When the supernatant was aspirated and dried, a powder sample could be obtained. The sample was used for $^1H$ NMR analysis. The results in FIG. 15 were obtained. As indicated in the results, a doublet peak around 1.4 ppm was observed, and the position was the same as that of the proton peak of the β-carbon in lactic acid, so that it was verified that the polysaccharide was lactated. No such lactation has commonly been observed in sugars.

Example 17

Chemically Crosslinked Sugar Derivative

Figure 16:
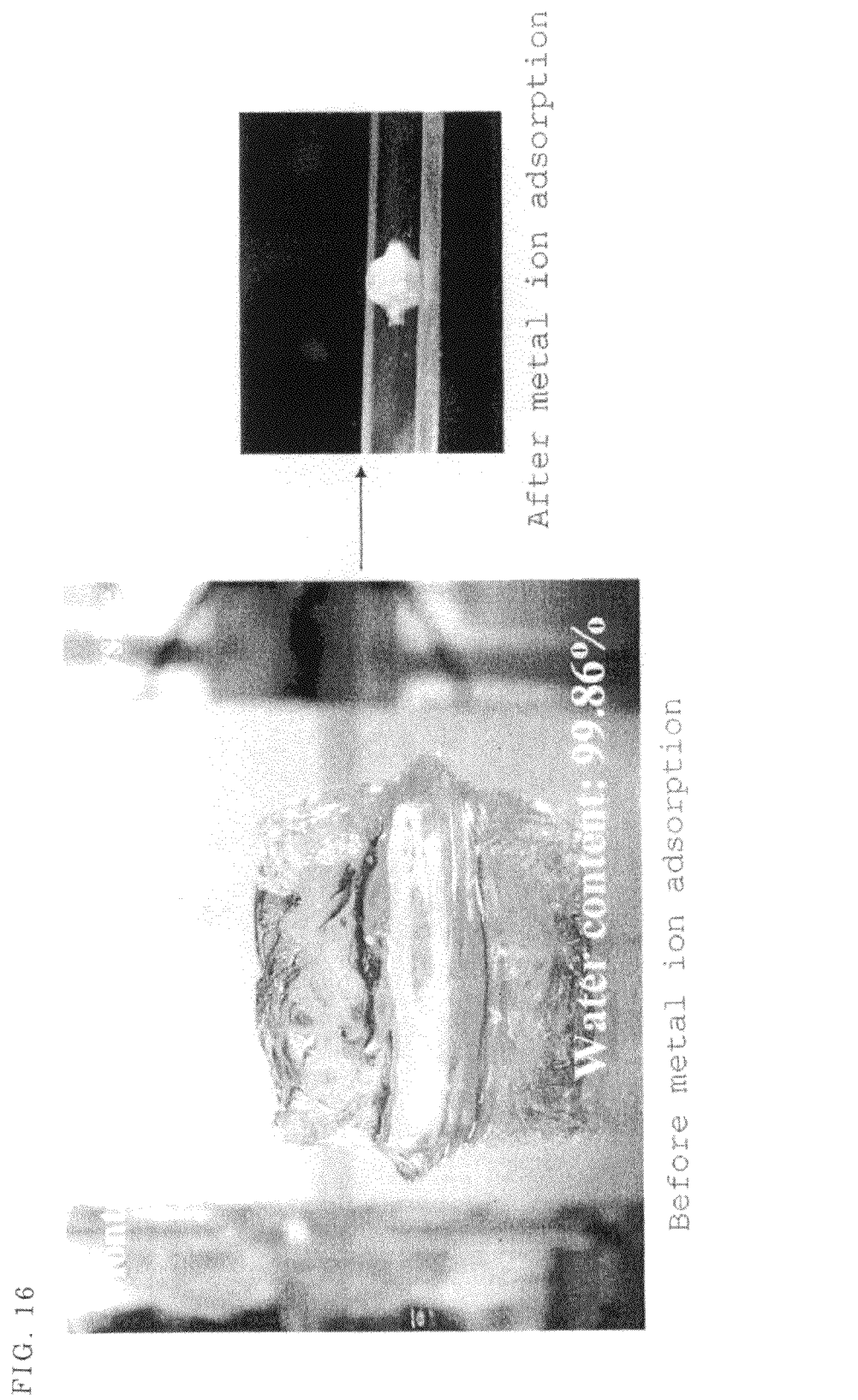
FIG. 16 shows the chemically crosslinked polysaccharide in gel in a photograph.

L-lysine as a diamine at an amount corresponding to 10 mol % of the monosaccharide unit moles in the polysaccharide was added at a state of aqueous solution, to an aqueous 0.5% solution of the polysaccharide obtained in Example 15, for reaction. Consequently, a chemically crosslinked polysaccharide was formed, to obtain a self-supporting gel transparent as shown in the photograph on the left side of FIG. 16. The water content in the gel was relatively high, namely 99.86%. When a metal ion (specifically, neodium ion) was adsorbed to the gel, then, the gel released water so that the gel shrank as shown in the photograph on the right side of FIG. 16.

Figure 17:
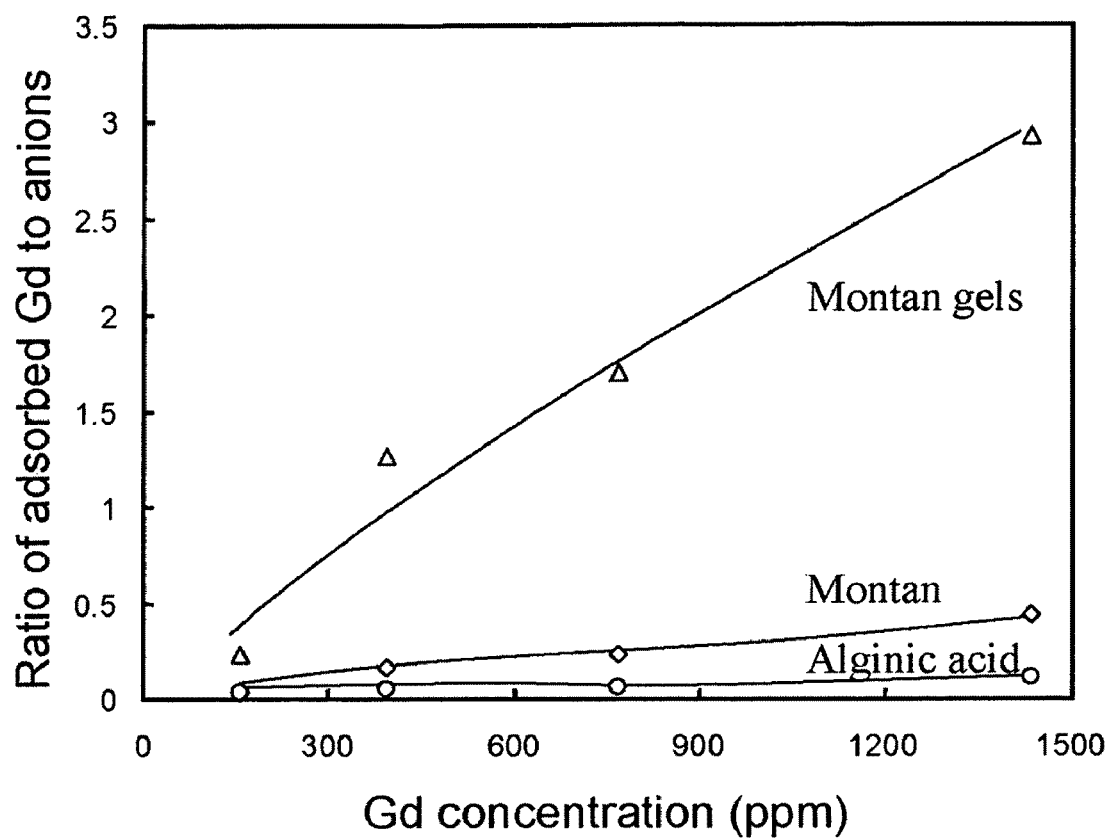
FIG. 17 shows the metal adsorption of the chemically crosslinked polysaccharide.

Subsequently, the polysaccharide gel, an aqueous 0.5% solution of the polysaccharide and an aqueous 0.5% solution of alginic acid were individually placed in an aqueous metal ion (gadolinium ion) solution, where the metal adsorption profile was measured by ICP (inductively coupled plasma method). The results are shown in FIG. 17. As apparently shown in FIG. 17, the polysaccharide gel (expressed as "Montan gels" in the figure) adsorbed an enormous amount of the metal ion. Compared with the polysaccharide without any reaction with diamine (aqueous polysaccharide solution: expressed as "Montan" in the figure), the adsorption level was about 10-fold at maximum on the basis of the minus ion number in the polysaccharide.

Example 18

Acetylation of Sugar Derivative

Figure 18:
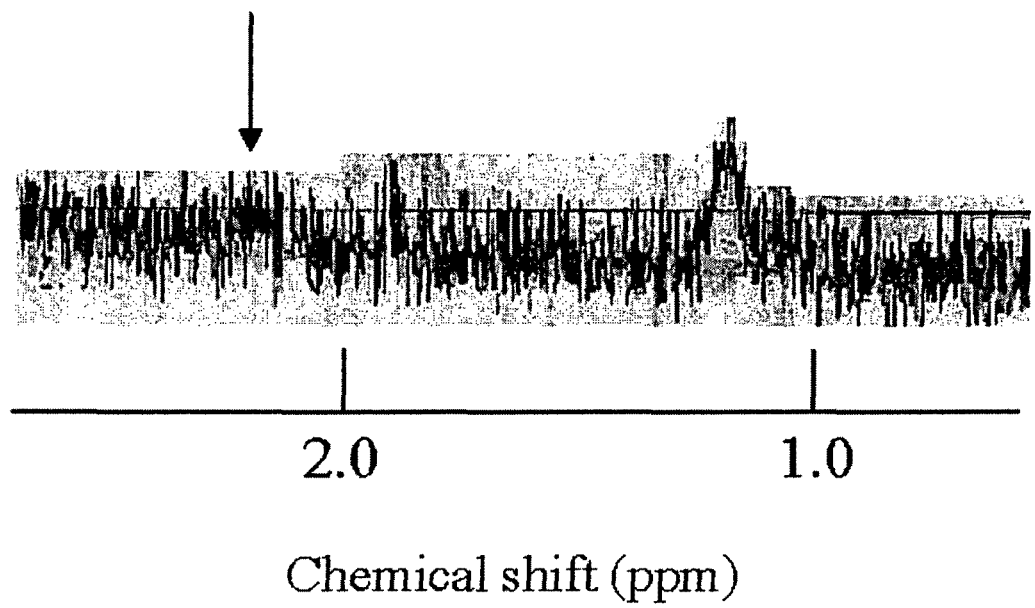
FIG. 18 shows the evidence of the acetylation of the polysaccharide.

By dissolving the polysaccharide obtained in Example 15 in DMSO for reaction with acetic anhydride, an acetylated polysaccharide with acetylated hydroxyl groups in the polysaccharide was prepared. The $^1$H NMR spectrum of the acetylated polysaccharide is shown in FIG. 18. At the position with an arrow in the figure, an acetylated (—OCOCH$_3$) proton signal can be observed.

Example 19

Modification of Sugar Derivative with Dye

Figure 19A:
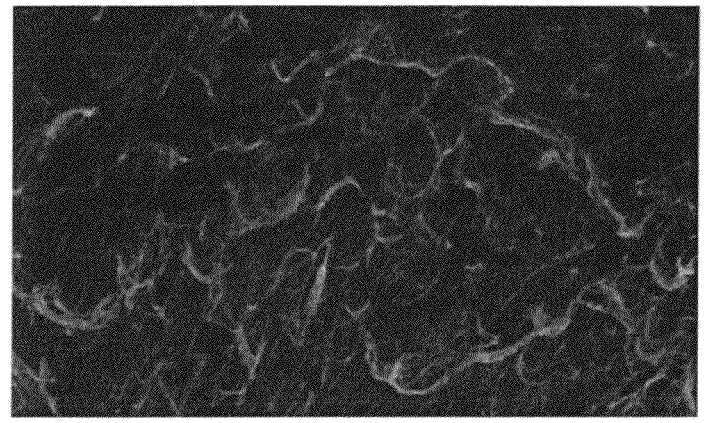
FIG. 19 shows a polysaccharide modified with a dye in a photograph.
Figure 19B:
Figure 19C:
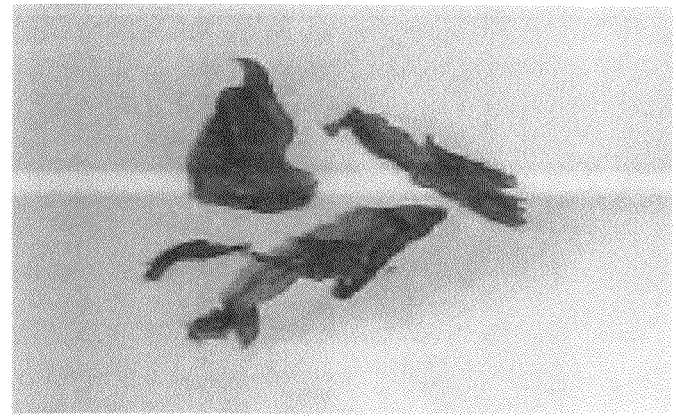

The polysaccharide obtained in Example 15 was treated individually with an amine-directed green fluorescence dye FITC, a cationic red dye Congo Red, and an anionic blue dye Prussian Blue. The fluorescence microscopic photographs of the polysaccharide modified with these dyes are shown in FIG. 19. The color photograph (a) shows the polysaccharide modified with FITC; the color photograph (b) shows the polysaccharide modified with Congo red; and the color photograph (c) shows the polysaccharide modified with Prussian Blue.

Example 20

Addition of Acidic Substance to Aqueous Sugar Derivative Solution

Figure 20:
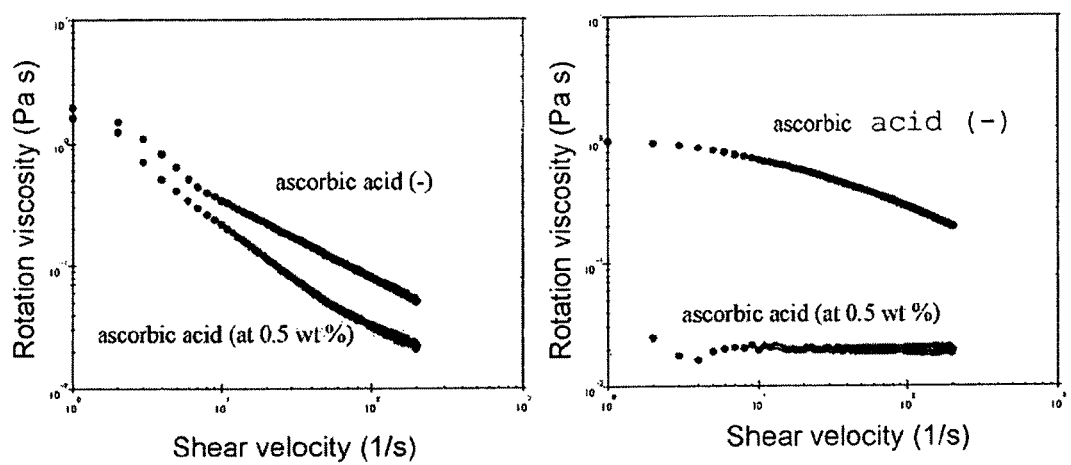
FIG. 20 shows the viscosity change of an aqueous polysaccharide solution with the addition of an acidic substance.

Preparing an aqueous solution of the polysaccharide obtained in Example 15 at 0.5% by weight and an aqueous solution of hyaluronic acid at 0.5% by weight, the rotation viscosity in unit Pa·s of these solutions was measured at individual shear velocities. Additionally, the same rotation viscosity of the individual aqueous solutions to which an aqueous solution of ascorbic acid at 0.5% by weight was preliminarily added was measured. The results of the measurement are shown in FIG. 20. On the left side of FIG. 20 are shown the results of the measurement of the aqueous solution of the polysaccharide while on the right side are shown the results of the measurement of the aqueous hyaluronic acid solution. In all the graphs, the graphs marked with "ascorbic acid (0.5 wt %)" shows the results with addition of the aqueous solution of ascorbic acid; and the graphs marked with "ascorbic acid (−)" shows the results with no addition of any aqueous solution of ascorbic acid.

Example 21

Polysaccharide Structure

Figure 21:
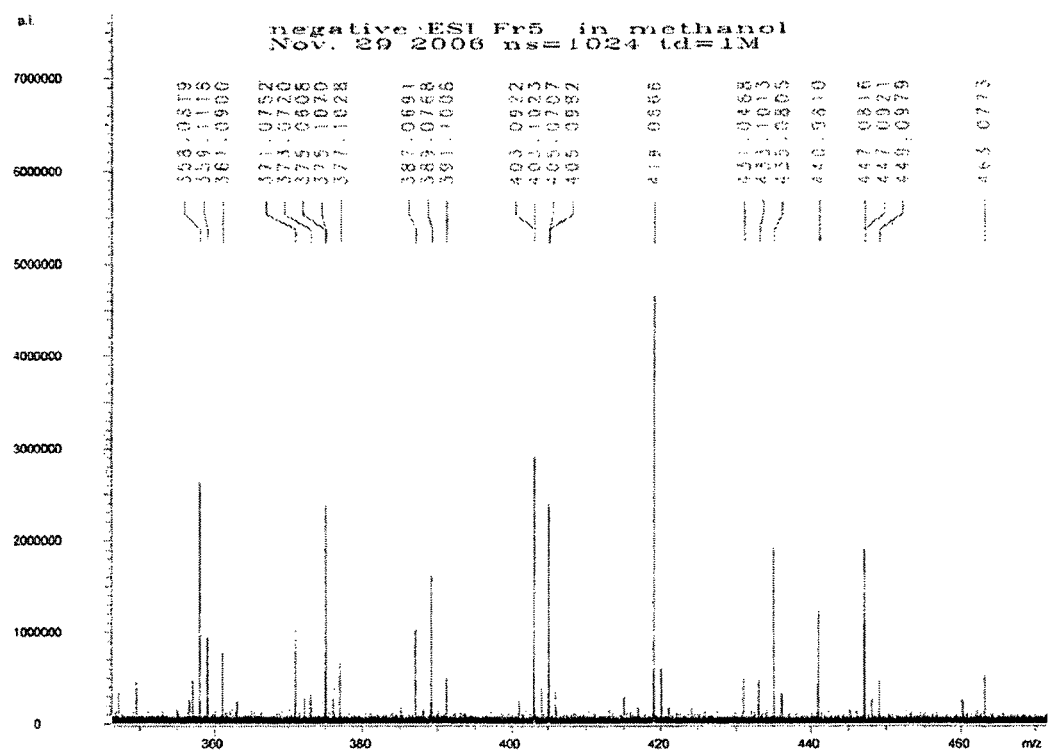

The polysaccharide obtained in Example 15 was treated with methanol and hydrochloric acid for acid decomposition, and the resulting products were analyzed on a high resolution ESI-MS spectrum. The resulting spectrum is shown in FIG. 21. The table in FIG. 22 collectively shows the molecular weights in the figure and molecular weights detected on other FT-MS spectra, which agree with those of certain sugars at several millimass levels. In the table in FIG. 22, the values in the column "m/z" show detected molecular weights; and values calculated by adding the atomic weight of hydrogen (1.0078) to the individual molecular weights are shown in the column "m/ztasuH (MS:1.0078).

In the table in FIG. 22, muramic acid could be identified from the entry Nos. 1, 3 and 8. From the entry Nos. 2, 3, 4, 6 and 7, the presence of sulfate group could be verified. From the entry No. 2, the presence of hexose was verified. From the entry No. 4, further, the presence of uronic acid was verified.

In the table in FIG. 22, additionally, the entry Nos. 1 through 4 were evidence for sugar constituents and also for the presence of sulfate group. The entry Nos. 5 and 6 verify that two continuous hexoses exist. The entry No. 7 verifies that uronic acid is adjacent to hexose. The entry No. 8 then shows that N-acetylmuramic acid exists adjacently to the two continuous hexoses. Three alignments of hexose-hexose-N-acetylmuramic acid can be identified as partial sequences. The sequence structure of the three sugars may possibly compose the repeat unit of the polysaccharide in the present Example, or a part of the repeat unit. However, it cannot be concluded definitely that the structure thereof composes the repeat unit or a part of the repeat unit.

The results in FIGS. 21 and 22 verify the presence of carboxylic acid (muramic acid, uronic acid), amide (muramic acid), hydroxyl group (all) and sulfate group.

Figure 23:
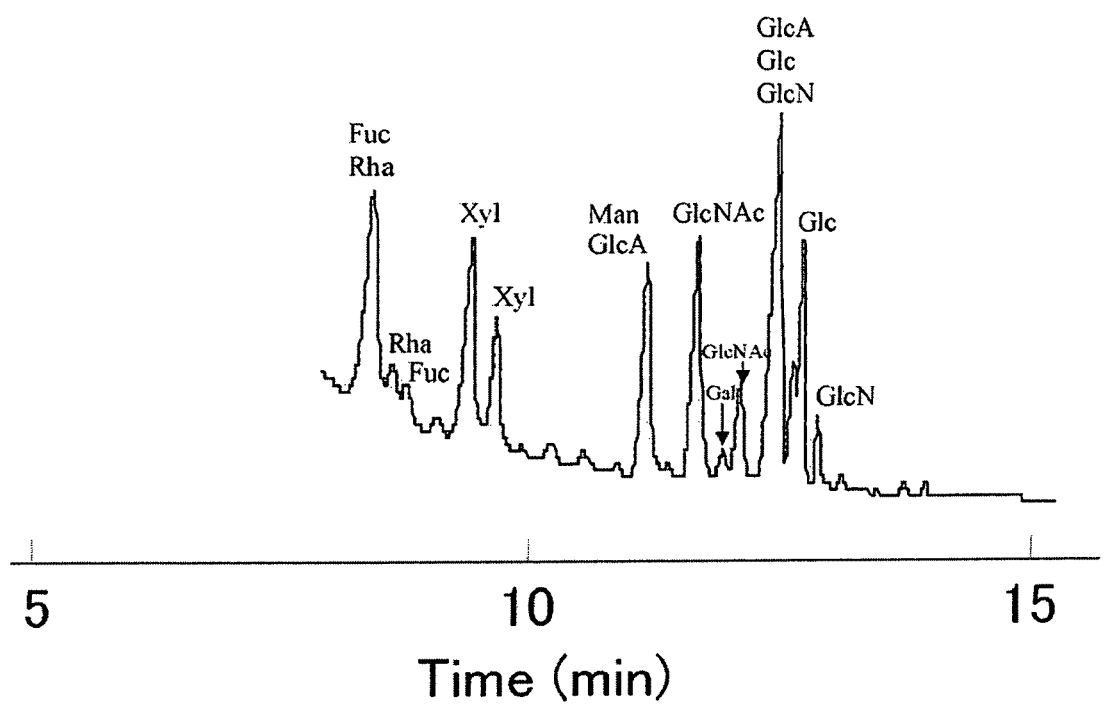
FIG. 23 shows the grounds for determining the sugars composing the polysaccharide.

Subsequently, the polysaccharide obtained in Example 15 was treated with hydrochloric acid/methanol at 70° C. over several days for decomposition; in case that the polysaccharide turned insoluble during the course, the solvents were additionally added if necessary for further decomposition; after the solvents were completely distilled off, the resulting mixtures were treated with a trimethylsilylation agent TMSI-C (as the product name) manufactured by GL Science, for gas chromatography while the treated mixtures remained as they were. The results are shown in FIG. 23. In FIG. 23, the presence of Fuc (fucose), Rha (rhamnose), Xyl (xylose), Ara (arabinose), Man (mannose), Glc (glucose), Gal (galactose), GlcA (glucuronic acid), GalA (galacturonic acid) and GalN (galactosamine) was confirmed as components of polysaccharide. Fucose and rhamnose) are 6-deoxy sugars. Xylose and arabinose are pentose with no 6-position. Glucose, mannose and galactose are hexose. Glucuronic acid and galacturonic acid are uronic acid. Glucosamine is a hexosamine.

Third Example Group

Example 22

Evaluation of Anti-Viral Activity

The anti-viral activities of individual samples of the polysaccharides (the sugar derivatives of the invention) as the subjects in the First Example Group and the Second Example Group against herpes simplex virus type 2 were determined by the plaque assay method. FIG. 24 shows the test results about the effect on suppressing the growth of herpes simplex virus type 2; FIG. 25 shows the test results about the inactivation effect of herpes simplex virus type 2. In FIGS. 24 and 25, the term "alkali-extracted sample" means the polysaccharide as the subject in the First Example Group; and the term "sample extracted at high pressure and high temperature" means the polysaccharide as the subject in the Second Example Group.

The reference of D. J. Shaeffel and V. S. Krylov as listed on "Ecotoxicology and Environmental Safety", Vol. 45, pp. 208-227 (2000) reports that the anti-viral activity is more prominent as the molecular weight gets larger and the sulfation degree is higher. As shown in FIGS. 24 and 25, the selection index as a marker of the anti-viral activity of the polysaccharide of the invention is at a very large value. It is generally defined that the selection index shown in the figures when the selection index exceeds 10 means the presence of anti-viral activity. For example, acyclovir as a conventional drug against herpes simplex virus type 2 is at a selection index of about 800.

INDUSTRIAL APPLICABILITY

In accordance with the invention, a sugar derivative derived from Aphanothece sacrum and with a novel polysaccharide structure is provided. Additionally, diverse applications for effectively utilizing the sugar derivative are also provided.

The invention claimed is:

1. A chemically crosslinked sugar derivative obtained via a reaction of a functional group of an isolated sugar derivative with a polyfunctional compound for crosslinking, the isolated sugar derivative isolated from a freshwater blue-green alga identified as Aphanothece sacrum, having a mean molecular weight of 2,000,000 or more and a repeat structure of a sugar chain unit containing a lactated, sulfated sugar as a sugar constituent, where a sugar constituent of a hexose structure and a sugar constituent of a pentose structure are conjugated together in a linear chain or a branched chain through an α-glycoside bond or a β-glycoside bond, where 2.7 or more hydroxyl groups per 100 hydroxyl groups are sulfated or sulfur element occupies 1.5% by weight or more of all of the elements in the sugar chain unit.

2. A sugar derivative-modified product obtained by modifying a functional group of an isolated sugar derivative with a compound for solubilization or functionalization or with a dye compound, the isolated sugar derivative isolated from a freshwater blue-green alga identified as Aphanothece sacrum, having a mean molecular weight of 2,000,000 or more and a repeat structure of a sugar chain unit containing a lactated, sulfated sugar as a sugar constituent, where a sugar constituent of a hexose structure and a sugar constituent of a pentose structure are conjugated together in a linear chain or a branched chain through an α-glycoside bond or a β-glycoside bond, where 2.7 or more hydroxyl groups per 100 hydroxyl groups are sulfated or sulfur element occupies 1.5% by weight or more of all of the elements in the sugar chain unit.

3. A polyion complex as a complex of an isolated sugar derivative with a polycation compound, the isolated sugar derivative isolated from a freshwater blue-green alga identified as Aphanothece sacrum, having a mean molecular weight of 2,000,000 or more and a repeat structure of a sugar chain unit containing a lactated, sulfated sugar as a sugar constituent, where a sugar constituent of a hexose structure and a sugar constituent of a pentose structure are conjugated together in a linear chain or a branched chain through an α-glycoside bond or a β-glycoside bond, where 2.7 or more hydroxyl groups per 100 hydroxyl groups are sulfated or sulfur element occupies 1.5% by weight or more of all of the elements in the sugar chain unit.

4. A liquid crystal gel as a polysaccharide-metal ion hybrid liquid crystal gel, obtained by putting an aqueous solution of an isolated sugar derivative having a concentration greater than 0.5 g/dl in contact with a polyvalent metal ion, where the polyvalent metal ion is one or more selected from ions of individual metals of Al, Se, Ti, V, Cr, Fe, Ga, Sr, Y, Zr, Nb, Ru, Rh, Pd, Cd, In, Ba, La, Hf, Ta, W, Re, Os, Ir, Hg, Pr, Bi, Ce, Nd, Sm, Eu, Gd, Tb, Dy, Ho, Er, Tm, Yb, Lu and U, the isolated sugar derivative isolated from a freshwater blue-green alga identified as Aphanothece sacrum, having a mean molecular weight of 2,000,000 or more and a repeat structure of a sugar chain unit containing a lactated, sulfated sugar as a sugar constituent, where a sugar constituent of a hexose structure and a sugar constituent of a pentose structure are conjugated together in a linear chain or a branched chain through an α-glycoside bond or a β-glycoside bond, where 2.7 or more hydroxyl groups per 100 hydroxyl groups are sulfated or sulfur element occupies 1.5% by weight or more of all of the elements in the sugar chain unit.

5. A liquid crystal gel as a polysaccharide-metal ion hybrid liquid crystal gel, obtained by putting an aqueous solution of a high concentration of a chemically crosslinked sugar derivative according to claim 1 in contact with a polyvalent metal ion.

* * * * *